US009982277B2

(12) United States Patent
Koshland et al.

(10) Patent No.: US 9,982,277 B2
(45) Date of Patent: May 29, 2018

(54) METHODS AND COMPOSITIONS FOR TARGET DNA MODIFICATION

(71) Applicant: The Regents of the University of California, Oakland, CA (US)

(72) Inventors: Douglas E. Koshland, Berkeley, CA (US); Lamia Wahba, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days. days.

(21) Appl. No.: 14/897,026

(22) PCT Filed: Jun. 10, 2014

(86) PCT No.: PCT/US2014/041728
§ 371 (c)(1),
(2) Date: Dec. 9, 2015

(87) PCT Pub. No.: WO2014/201015
PCT Pub. Date: Dec. 18, 2014

(65) Prior Publication Data
US 2016/0138045 A1    May 19, 2016

Related U.S. Application Data

(60) Provisional application No. 61/833,798, filed on Jun. 11, 2013.

(51) Int. Cl.
*C12N 5/00* (2006.01)
*C12N 15/90* (2006.01)
*C12N 15/10* (2006.01)

(52) U.S. Cl.
CPC ......... *C12N 15/902* (2013.01); *C12N 15/102* (2013.01); *C12N 15/905* (2013.01)

(58) Field of Classification Search
CPC ......... C12N 5/902; C12N 5/905; C12N 5/102
See application file for complete search history.

(56) References Cited

U.S. PATENT DOCUMENTS

| | | |
|---|---|---|
| 8,697,359 B1 | 4/2014 | Zhang |
| 2005/0210539 A1 | 9/2005 | Heintz et al. |
| 2011/0059160 A1 | 3/2011 | Essner et al. |
| 2014/0068797 A1 | 3/2014 | Doudna et al. |

FOREIGN PATENT DOCUMENTS

| | | |
|---|---|---|
| WO | WO 2012/116274 A2 | 8/2012 |
| WO | WO 2013/176772 | 11/2013 |
| WO | WO 2014/093595 | 6/2014 |

OTHER PUBLICATIONS

Li et al. Nature Biotechnology 31(8):681-683, Aug. 2013.*
Dow. Trends in Molecular Medicine 21(10):609-621, 2015.*
Gao et al. Genome Biology 18:1-15, 2017.*
Hsu et al. Cell 157:1262-1278, Jun. 2014.*
Mittelman, et al.; "Zinc-finger directed double-strand breaks within CAG repeat tracts promote repeat instability in human cells"; PNAS; vol. 106, No. 24, pp. 9607-9612 (Jun. 16, 2009).
Chylinski, et al.; "The tracrRNA and Cas9 families of type II CRISPR-Cas immunity systems"; RNA Biology; vol. 10, No. 5, pp. 726-737 (May 2013).
Cong, et al.; "Multiplex Genome Engineering Using CRISPR/Cas Systems"; Sciencexpress; http://www.sciencemag.org/content/early/recent; doi: 10.1126/science.1231143; 7 pages (Jan. 3, 2013).
Cong, et al.; "Supplementary Materials for Multiplex Genome Engineering Using CRISPR/Cas Systems"; Science; www.sciencemag.org/cgi/content/full/science.12231143/DC1; doi: 10.1126/science.1231143; 26 pages (Jul. 5, 2012).
GenBank AAK33936, conserved hypothetical protein [*Streptococcus pyogenes* M1 GAS] Mar. 12, 2007 [online]. [Retrieved on Sep. 2, 2014]. Retrieved from the Internet: <URL: http://www.ncbi.nlm.nih.gov/protein/13622193?sat=18&satkey=1856166>.
GenBank CAG38796.1, RAD51 [*Homo sapiens*] Oct. 16, 2008 [online]. [Retrieved on Sep. 2, 2014]. Retrieved from the Internet: <URL: http://vvww.ncbi.nlm.nih.gov/protein/CAG38796>.
Hilario, et al.; "Direct imaging of human Rad51 nucleoprotein dynamics on individual DNA molecules"; Proc. Natl. Acad. Sci. USA; vol. 106, No. 2, pp. 361-368 (Jan. 13, 2009).
Jinek, et al.; "A Programmable Dual-RNA—Guided DNA Endonuclease in Adaptive Bacterial Immunity"; Science; vol. 337, pp. 816-821 (Aug. 17, 2012).
Jinek, et al.; "Supplementary Materials for a Programmable Dual-RNA—Guided DNA Endonuclease in Adaptive Bacterial Immunity"; Science; www.sciencemag.org/cgi/content/full/science.1225829/DC1; 37 pages (Jun. 28, 2012).
Jinek, et al.; "RNA-programmed genome editing in human cells"; eLIFE; vol. 2, pp. 1-9 (Jan. 29, 2013).
Mali, et al.; "RNA-Guided Human Genome Engineering via Cas9"; Sciencexpress; http://www.sciencemag.org/contert/early/recent; doi: 10.1126/science.1232033; 5 pages (Jan. 3, 2013).
Mali, et al.; "Supplementary Materials for RNA-Guided Human Genome Engineering via Cas9"; Science; www.sciencemag.org/cgi/content/full/science.1232033/DC1; doi: 10.1126/science.1232033; 35 pages (Jan. 3, 2013).
UniProt Q99ZW2, CRISPR-associated endonuclease Cas9/Csn1, Accession No. Q99ZW2, Sequence Last modified: Jun. 1, 2001-v1 [online]. [Retrieved on Sep. 26, 2014]. Retrieved from the Internet: <URL: http://www.uniprot.org/uniprot/Q99ZW2> pp. 1-17.
Yanez, et al.; "Gene targeting is enhanced in human cells overexpressing hRAD51"; Gene Ther.; vol. 6, No. 7, pp. 1282-1290 (1999).

* cited by examiner

*Primary Examiner* — Marcia S Noble
(74) *Attorney, Agent, or Firm* — Bozicevic Field & Francis, LLP; Paula A. Borden; Otto C. Guedelhoefer

(57) ABSTRACT

The disclosure provides compositions and methods for increasing efficiency of Cas9-mediated target DNA modification. Specifically, the disclosure provides compositions and methods for carrying out site-directed modification of a target DNA, the methods comprising contacting the target DNA with: a) a complex comprising a Cas9 polypeptide and a guide RNA, and b) a Rad51 polypeptide. The site-directed modification of a target DNA can be carried out in a living cell in vitro, in a living cell in vivo, or in a cell-free system in vitro.

7 Claims, 34 Drawing Sheets

FIGURE 1
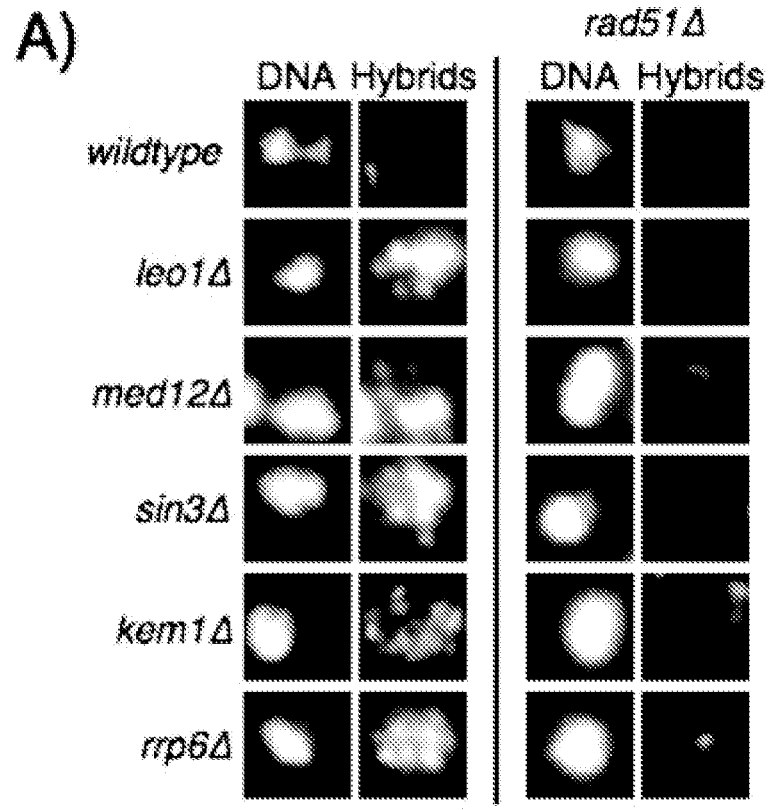
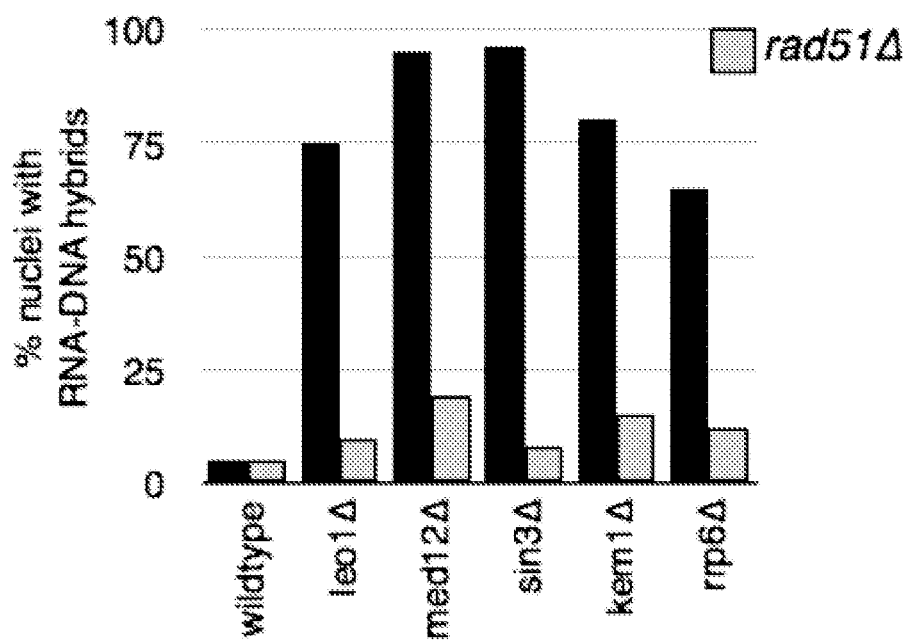

FIGURE 2
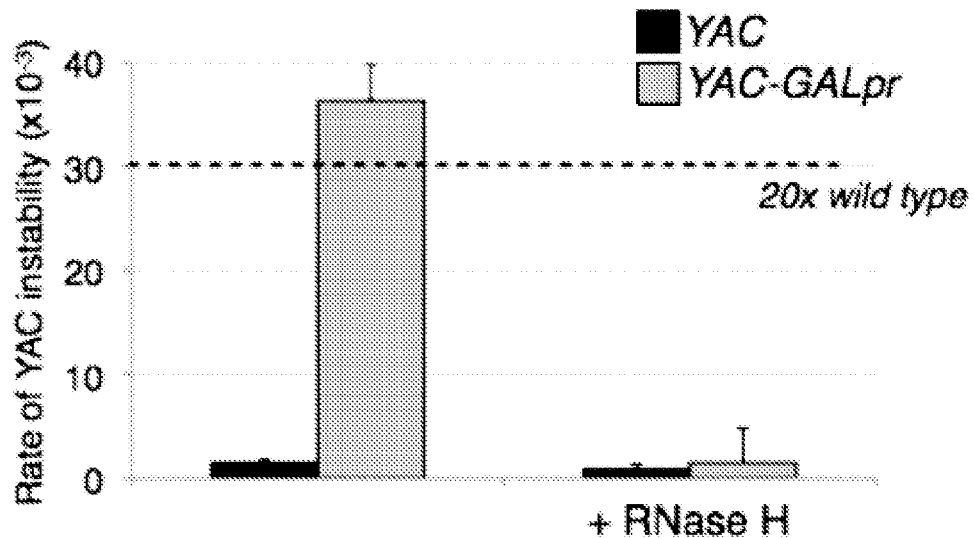
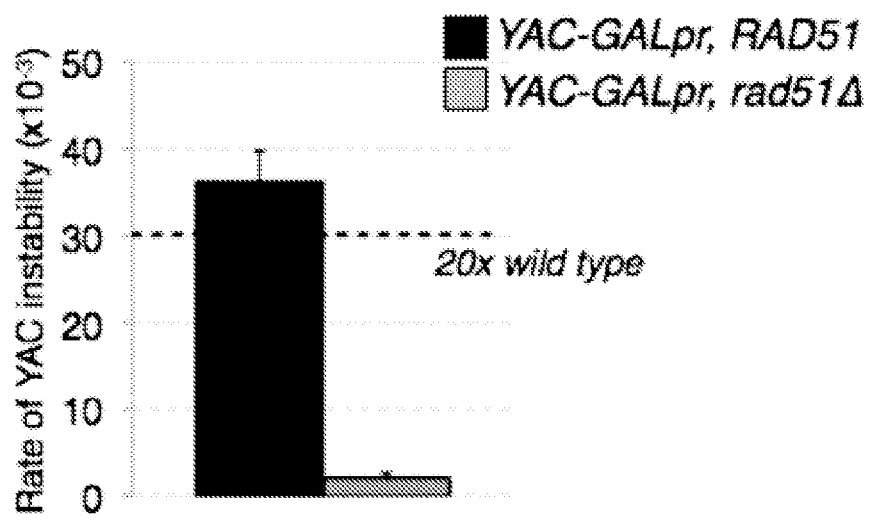

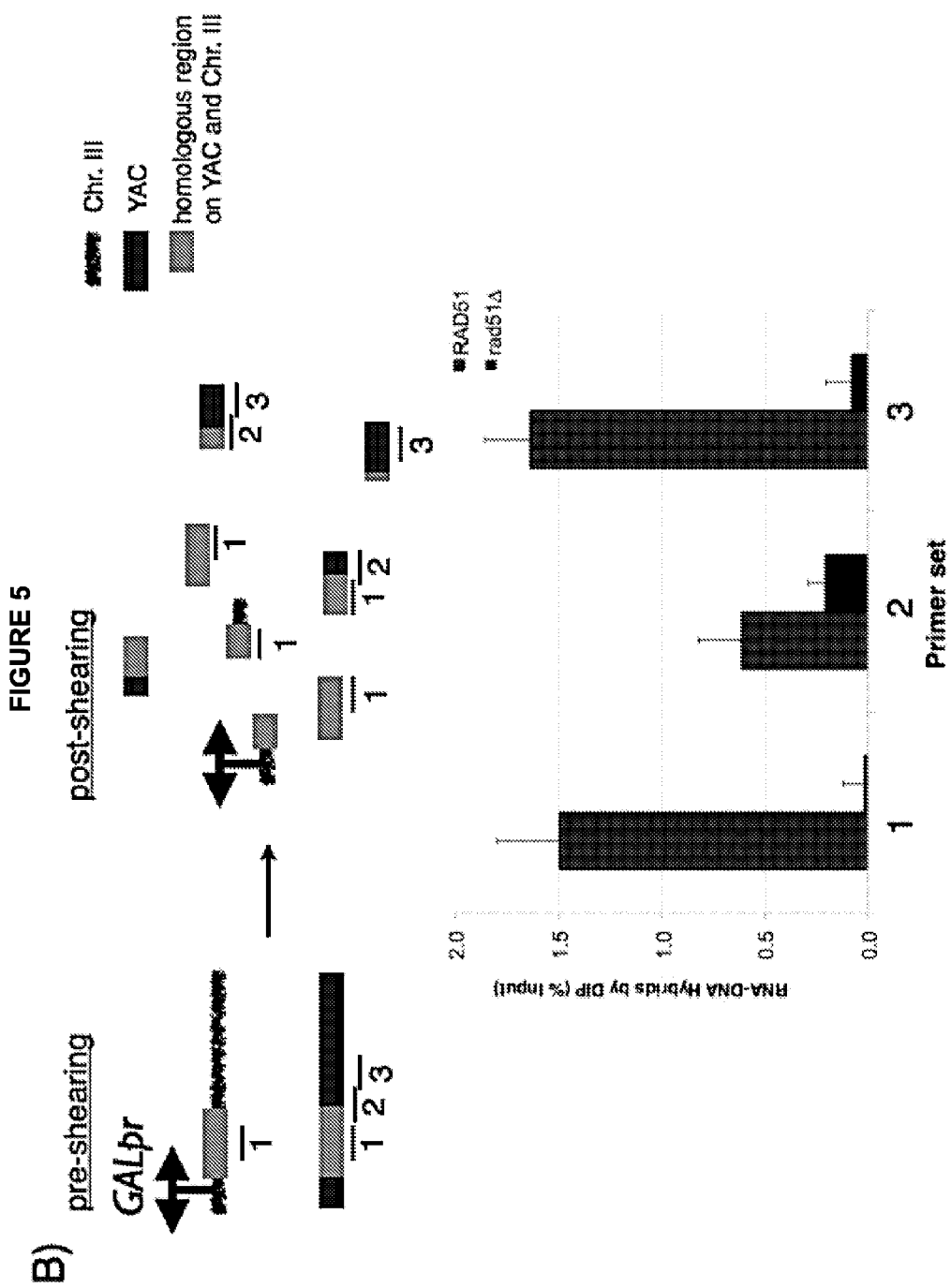

FIGURE 8
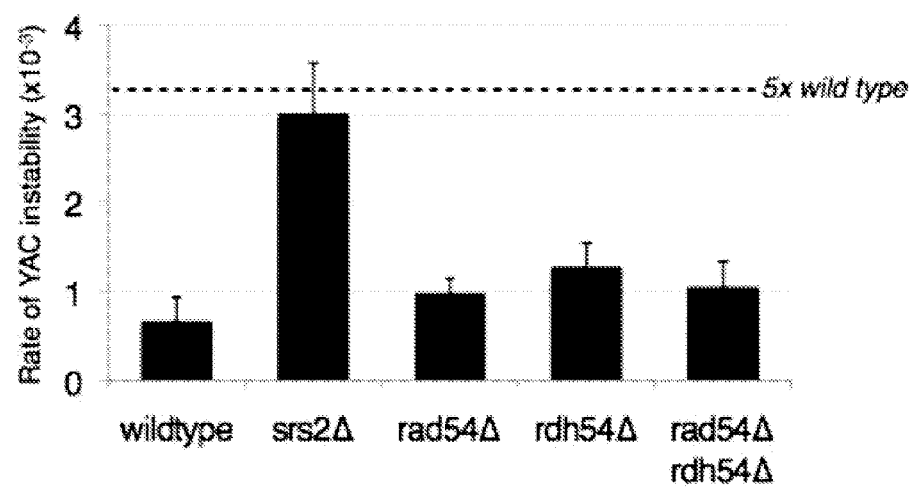
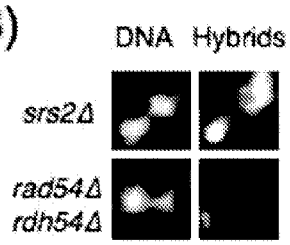

FIGURE 8
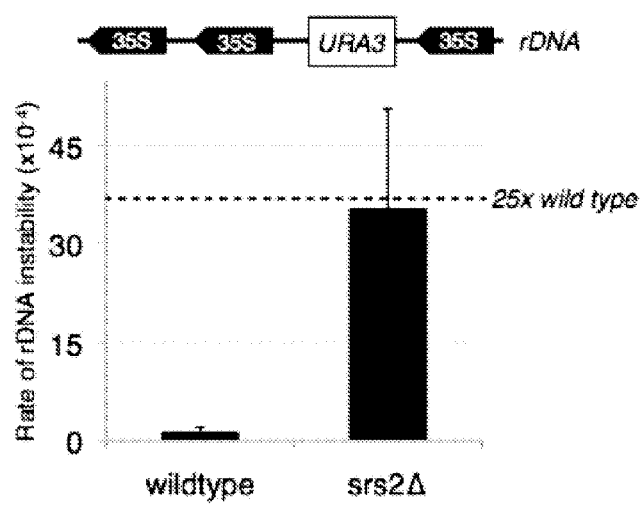

FIGURE 17
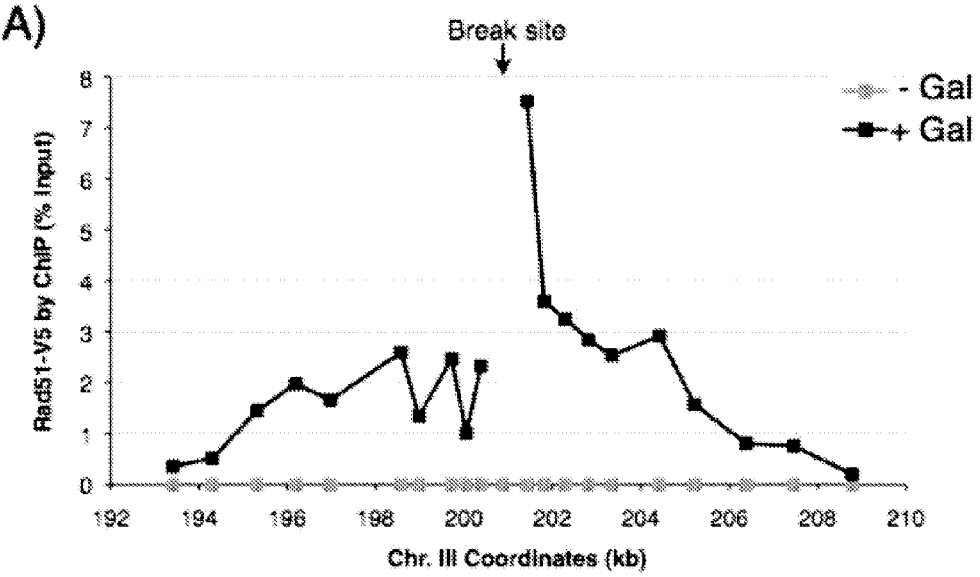
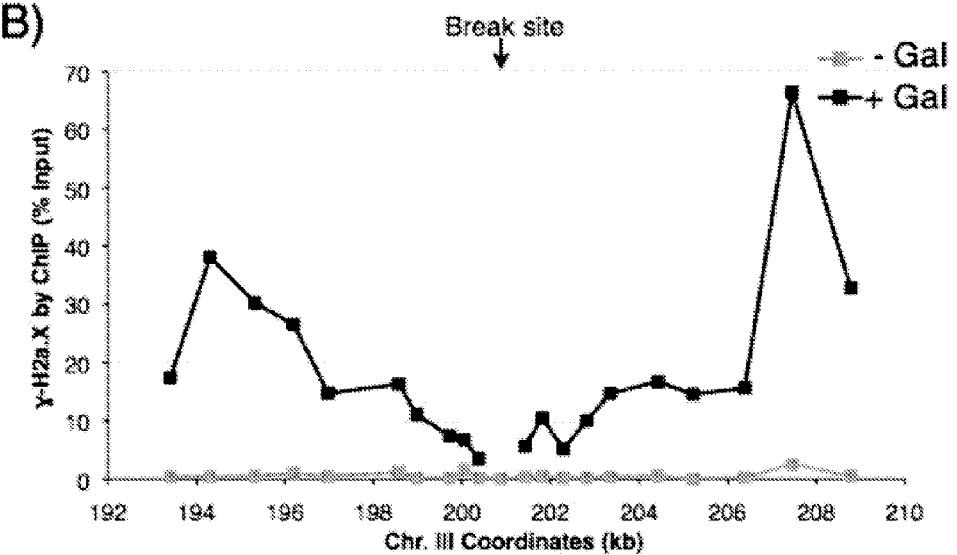

FIGURE 22
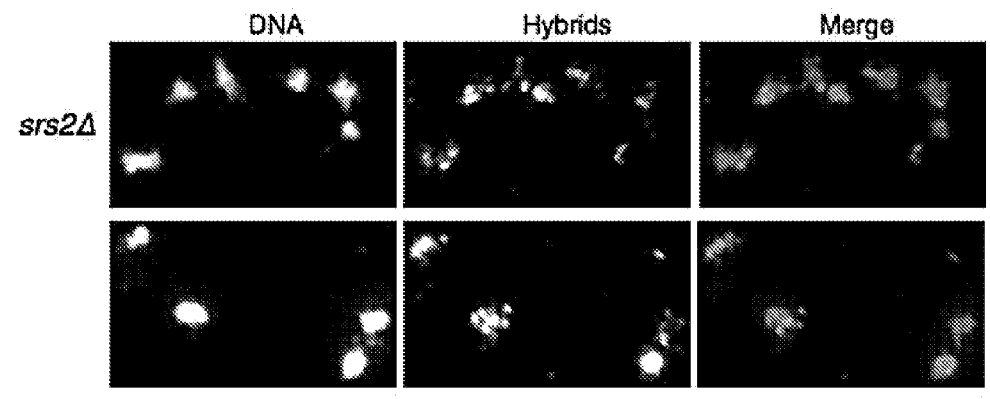
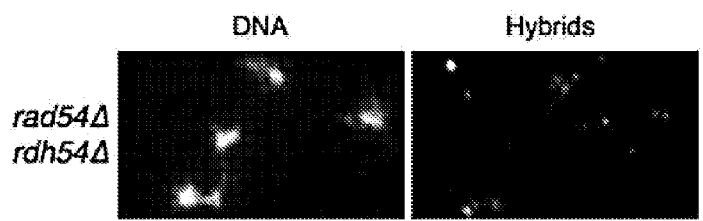
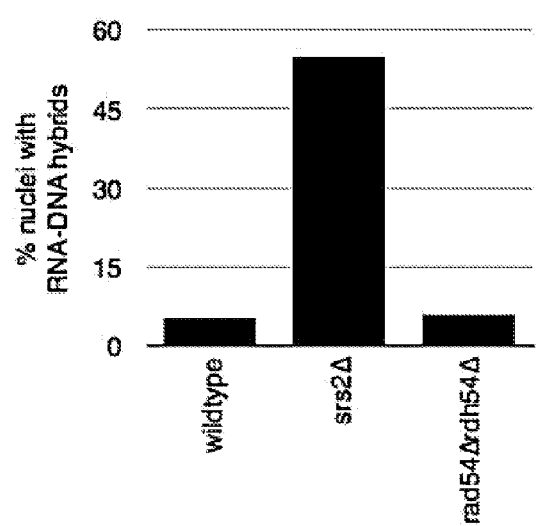

Figure 23

Cas9 *Streptococcus pyogenes*

7-166:     RuvC endonuclease domain motif 1
731-790:   RuvC endonuclease domain motif 2
949-1003:  RuvC endonuclease domain motif 3
791-948:   HNH endonuclease domain Total length = 1368

>Streptococcus_pyogenes_M1_GAS| gi|13622193|gb|AAK33936.1|

MDKKYSIGLDIGTNSVGWAVITDEYKVPSKKFKVLGNTDRHSIKKNLIGALLFDSGETAEATRLK
RTARRRYTRRKNRICYLQEIFSNEMAKVDDSFFHRLEESFLVEEDKKHERHPIFGNIVDEVAYHE
KYPTIYHLRKKLVDSTDKADLRLIYLALAHMIKFRGHFLIEGDLNPDNDVDKLFIQLVQTYNQLF
EENPINASGVDAKAILSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTEITKAPLSASMIKRYD
EHHQDLTLLKALVRQQLPEKYKEIFFDQSKNGYAGYIDGGASQEEFYKFIKPILEKMDGTEELLV
KLNREDLLRKQRTFDNGSIPHQIHLGELHAILRRQEDFYPFLKDNREKIEKILTFRIPYYVGPLA
RGNSRFAWMTRKSEETITPWNFEEVVDKGASAQSFIERMTNFDKNLPNEKVLPKHSLLYEYFTVY
NELTKVKYVTEGMRKPAFLSGEQKKAIVDLLFKTNRKVTVKQLKEDYFKKIECFDSVEISGVEDR
FNASLGTYHDLLKIIKDKDFLDNEENEDILEDIVLTLTLFEDREMIEERLKTYAHLFDDKVMKQL
KRRRYTGWGRLSRKLINGIRDKQSGKTILDFLKSDGFANRNFMQLIHDDSLTFKEDIQKAQVSGQ
GDSLHEHIANLAGSPAIKKGILQTVKVVDELVKVMGRHKPENIVIEMARENQTTQKGQKNSRERM
KRIEEGIKELGSQILKEHPVENTQLQNEKLYLYYLQNGRDMYVDQELDINRLSDYDVDHIVPQSF
LKDDSIDNKVLTRSDKNRGKSDNVPSEEVVKKMKNYWRQLLNAKLITQRKFDNLTKAERGGLSEL
DKAGFIKRQLVETRQITKHVAQILDSRMNTKYDENDKLIREVKVITLKSKLVSDFRKDFQFYKVR
EINNYHHAHDAYLNAVVGTALIKKYPKLESEFVYGDYKVYDVRKMIAKSEQEIGKATAKYFFYSN
IMNFFKTEITLANGEIRKRPLIETNGETGEIVWDKGRDFATVRKVLSMPQVNIVKKTEVQTGGFS
KESILPKRNDKLIARKKDWDPKKYGGFDSPTVAYSVLVVAKVEKGKSKKLKSVKELLGITIMERS
SFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPI
REQAENIIHLFTLTNLGAPAAFKYFDTTIDRKRYTSTKEVLDATLIHQSITGLYETRIDLSQLGG
D

Figure 24

GenBank

```
  1 mamqmqlean adtsveeesf gpqpisrleq cginandvkk leeagfhtve avayapkkel
 61 inikgiseak adkilaeaak lvpmgfttat efhqrrseii qittgskeld kllqggietg
121 sitemfgefr tgktqichtl avtcqlpidr gggegkamyi dtegtfrper llavaerygl
181 sgsdvldnva yarafntdhq tqllyqasam mvesryalli vdsatalyrt dysgrgelsa
241 rqmhlarflr mllrladefg vavvitnqvv aqvdgaamfa adpkkpiggn iiahasttrl
301 ylrkgrgetr ickiydspcl peaeamfain adgvgdakd
```

GenBank CAG38796

339 amino acids

FIGURE 25

ChIP Primers

| | Reverse Primer sequence | midpoint of primer (bp) | Forward Primer sequence | midpoint of primer (bp) | product size (bp) | midpoint of primer set in bp | product spacing (bp) |
|---|---|---|---|---|---|---|---|
| YAC52 | GAG AGG CTG AGG CAG GAG | 307310 | CAG GTT CTT GTT GAT AAG GC | 307508 | 198 | 307409 | — |
| YAC51 | GAA GAT AGA ACC CTG AAG TCC | 308263 | ATA GCA CAC ATC AAG TGG TG | 308539 | 276 | 308401 | 992 |
| YAC50 | TGA CCT CTC TCC CCA AAC | 309232 | TCC TTC CTT TTC CCC TC | 309443 | 211 | 309337.5 | 936.5 |
| YAC49 | GCC AAT AGT AAG CAA GCA G | 310455 | CAA AGA CAA GGT TTC ATT TTC | 310543 | 110 | 310499 | 1162.5 |
| YAC48 | AGA GCA ATC AGA AAA TGG TAG | 311066 | CAA ATG AGA AAA ATA AGG TGT GTG | 311216 | 150 | 311141 | 651 |
| YAC47 | TGC TCA CCT ACA TTT CCT G | 311327 | ATC TTG GCA ACG GAC TGC | 311471 | 144 | 311399 | 1298 |
| YAC46 | GAC TAA AGA CCT TCC GTT TG | 312344 | CAG CCA AGA ATA AGC CTA TC | 312558 | 214 | 312451 | 1052 |
| YAC45 | TTT GTG TCA GGA ACT AAA CAA C | 314239 | GAA TAA AAC TTA CTG TCA TCC ATC | 314495 | 166 | 314432 | 961 |
| YAC44 | GTG ATG AGG CTG GCA GTG | 315187 | CCA TAC TTA TTT GGA GAT TGC | 315428 | 241 | 315307.5 | 895.5 |
| YAC43 | CAA ATA CTT CTA CAC ATC ATC CC | 316074 | GAA AAC ATA ACA GCA TTC CC | 316208 | 134 | 316141 | 833.5 |
| YAC42 | TTG CTG GAT TCT ATT TCT C | 317323 | ACT TTT ATT TCT GAA CTG AAC TGT TGG | 317555 | 232 | 317439 | 1298 |
| YAC41 | TGA AGG AAA CAA AAC CAA AG | 318276 | CCA AGC CAC TGG AAT AAA G | 318514 | 238 | 318395 | 956 |
| YAC-10 F-R | CCA AAT GCT TCC CCT CTC TT | 319029 | GAG GCG GAA GGT GTA GTG AG | 319261 | 232 | 319145 | 750 |
| YAC-9 F-R | TGT CCC CTG TAT TAA GGC ATT T | 319602 | TGG TTT CAT CTC AAG TTT TCC A | 319762 | 160 | 319682 | 537 |
| YAC-8 F-R | TCA GCT ATC CAC CCT TGA CC | 320099 | TGT TGC CAA ATA AAG AGA AAC AAA | 320279 | 180 | 320189 | 507 |
| YAC-7 F-R | TGC AAC CTT ATT TTT CAG TTC C | 320595 | CCG CAT CTT CCT TTT GTA GC | 320765 | 170 | 320680 | 491 |
| YAC-6 F-R | GGA GGG ACC CTG TCC ATC TA | 321062 | CAT TTT TTC AAC AAG AGC ATG TA | 321270 | 208 | 321166 | 486 |
| YAC-5 F-R | GGG AAC TAA ATG TGT AGG TGG T | 321544 | GAG AGG ATG CTG CAA AGA GC | 321759 | 215 | 321651.5 | 485.5 |
| YAC-4 F2-R2 | AGA GTT CCA GGG CTG TCA AA | 321958 | TCA GGA AGG ATG ATG AAG ACC AGA | 322187 | 229 | 322072.5 | 421 |
| YAC-3a F-R | TAT GGA ATT CAA CTT ACC TTC | 322432 | AGG GAA TGG AGA CAT AAA CC | 322649 | 217 | 322540.5 | 468 |
| YAC-3 F2-R2 | TGG ATG CAG TAG TGG GGA GT | 322877 | TGC AGG AAA CCT GGA AAC AT | 323102 | 225 | 322989.5 | 449 |
| YAC-2 F-R | GTT AGG ATT TGC CAC TGA GG | 323365 | CCA CCG GCA CCT CCC GCA GG | 323613 | 250 | 323488 | 498.5 |
| YAC-1a F-R | ACC TCT GGC TGG AGG TCA C | 323828 | CAG GGC ATG CTC ATG TAG AG | 324025 | 147 | 323921.5 | 463.5 |
| YAC-1 F2-R2 | TGG TCG CTA TAC TGC TGT CG | 324222 | GCC TGA TGC GGT ATT TTC TC | 324414 | 192 | 324318 | 366.5 |
| YAC 0 F-R | TGC AAG GCG ATT AAG TTG GG | 324506 | CCC GCT CGG CGG CTT CTA ATC | 324771 | 265 | 324638.5 | 320.5 |
| YAC 1 F-R | GAG GCA TTA AAC ACA TGG TAG | 325373 | GAG GAA ATG AGC TGC ATT TTC | 325619 | 246 | 325496 | 857.5 |
| YAC 2 F-R | CTA AAT CTT CAT TGC TGC AC | 325620 | GAA AAT GTG CTA GGC ACC GTA C | 325871 | 251 | 325745.5 | 249.5 |

FIGURE 25 (cont.)

| | Reverse Primer sequence | midpoint of primer (bp) | Forward Primer sequence | midpoint of primer (bp) | product size (bp) | midpoint of primer set in bp | product spacing (bp) |
|---|---|---|---|---|---|---|---|
| YAC 3 F2-R2 | AGG CAA GTA AGC CTT TTC CA | 325916 | CAA GCA TGC CAT AAA TGT TCA | 326104 | 188 | 326010 | 264.5 |
| YAC 4 F-R | CAT AAT GTC CCT AAT CCT ACC | 326139 | CCC ATA TTT CCC CAA ATA AAG | 326424 | 285 | 326281.5 | 371.5 |
| YAC 5 F-R | TAG CCC TTT TCA GAC TCT GC | 326595 | AGC CAA TCT ACA GAC TGG CC | 326843 | 248 | 326719 | 457.5 |
| YAC 6 F2-R2 | TAG GTC AAT GCA GCA TCA GC | 327060 | TGG ATG TCT GGA AAA CAG CA | 327283 | 223 | 327171.5 | 452.5 |
| YAC 7 F-R | GTT ACC AAA TCT TTC TAA GC | 327573 | AGG CAA CAA ACA TCA AAT GG | 327835 | 262 | 327704 | 532.5 |
| YAC 8 F-R | TGT TTT GGT AAA CAT TAG GC | 328106 | GAG GAA TCT CAC ATG TAG AG | 328172 | 266 | 328139 | 535 |
| YAC 9 F2-R2 | TGC TCA AAT TCC TTT CAG TCA A | 329050 | TGC GTA CGA TGC ACT AGG AA | 329297 | 247 | 329173.5 | 934.5 |
| YAC 10 F2-R2 | TGG TGC CCC GTT TAT AAC TC | 330062 | AAA GCC AGT GGC AAA AGA GA | 330260 | 199 | 330160.5 | 987 |
| YAC 11 F2-R2 | GGA CCA GGC TTG ACA ATG AT | 331359 | ATT CCA AGG CCA AGC ATA GA | 331581 | 222 | 331470 | 1309.5 |

YAC Integration primers

Forward: CAA TAC CAA GGA TCC CTT TAG CTC TTA AAG AGA GAC GAC AGG ATA GCA CAG ATG GTC GAC TCT AGA GGA TCC Reverse: TAT GTG CAG CAG GAT ATT GGC TGT GCT GTT AGA CAA ATC CTT CTG TAC TCC AGA CCT GCG AGC AGG GAA A

METHODS AND COMPOSITIONS FOR TARGET DNA MODIFICATION

CROSS-REFERENCE

This application claims the benefit of U.S. Provisional Patent Application Nos. 61/833,798, filed Jun. 11, 2013, which application is incorporated herein by reference in its entirety.

INTRODUCTION

The present disclosure is in the field of site-directed modification of target DNA.

REFERENCES

Chylinski et al. (2013) *RNA Biol.* 10:726; Jinek et al. (2012) *Science* 337:816; Mali et al. (2013) *Science* 339:823; and Cong et al. (2013) *Science* 339:819

SUMMARY

The present disclosure provides compositions and methods for increasing efficiency of Cas9-mediated target DNA modification.

BRIEF DESCRIPTION OF THE DRAWINGS

FIG. 8. Deletion of SRS2, but not RAD54 and RDH54 increases genome instability and hybrid formation.

FIG. 17. Rad51 and γ-H2a.X binding at an inducible break site on Chromosome III.

FIG. 22. Larger panels of chromatin spreads showing multiple nuclei of srs2Δ and rdh54Δrad54Δ mutants stained with S9.6 antibody.

FIG. 23 depicts an amino acid sequence of a Cas9/Csn1 protein from *Streptococcus pyogenes*. SEQ ID NO:1.

FIG. 24 depicts an amino acid sequence of a Rad51 polypeptide. SEQ ID NO:2.

FIG. 25 provides Table 2. From top to bottom, left to right, SEQ ID NOs:3-76.

DEFINITIONS

Figure 1:
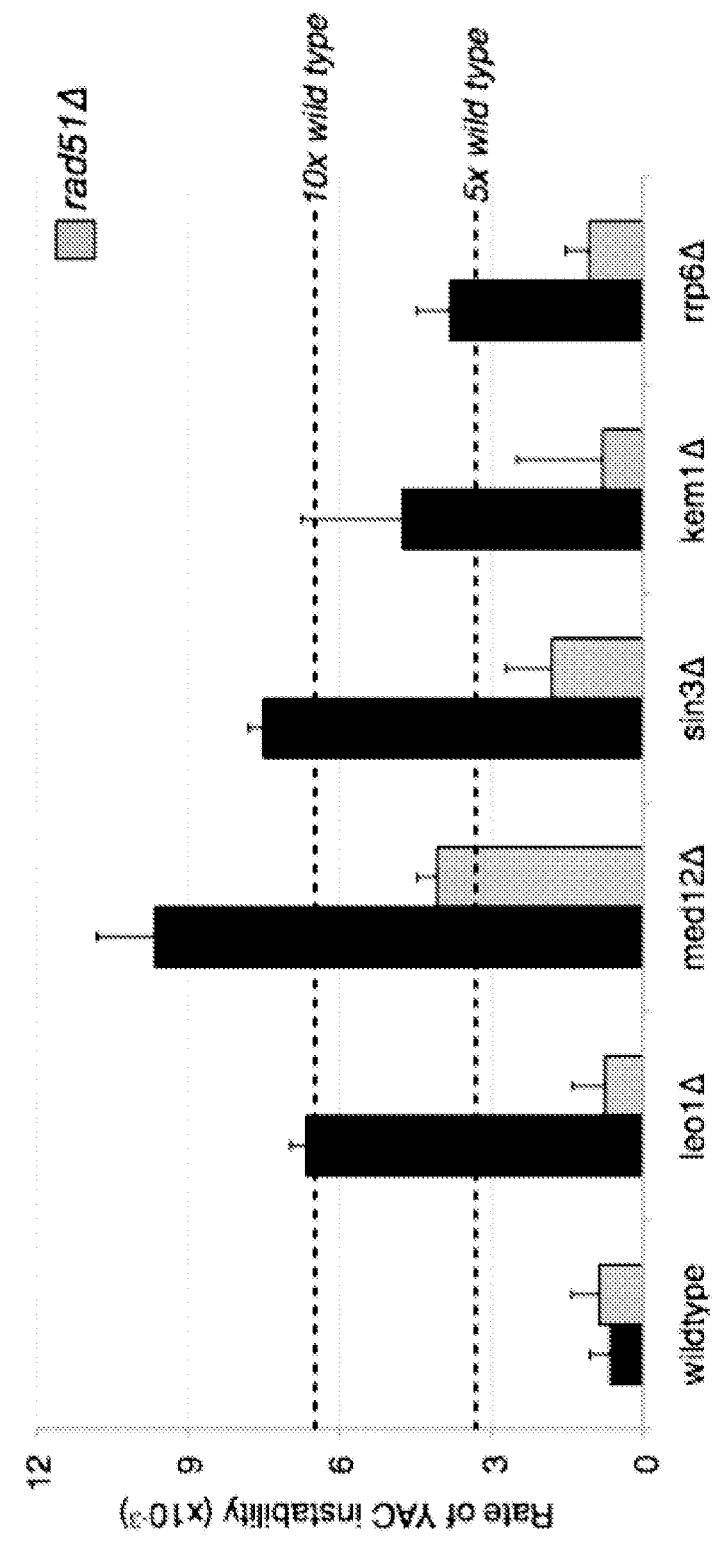
FIG. 1. Deletion of RAD51 suppresses RNA-DNA hybrids and YAC instability.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C) [DNA, RNA]. In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a subject DNA-targeting RNA molecule is considered complementary to a uracil (U), and vice versa. As such, when a G/U base-pair can be made at a given nucleotide position a protein-binding segment (dsRNA duplex) of a subject DNA-targeting RNA molecule, the position is not considered to be noncomplementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide) refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., DNA-targeting RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

A "host cell," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

The terms "individual," "subject," "host," and "patient," are used interchangeably herein and refer to any mammalian subject for whom diagnosis, treatment, or therapy is desired, particularly humans.

The term "guide RNA" as used herein refers to the molecule that binds to the Cas9 polypeptide and targets the polypeptide to a specific location within the target DNA and may also be referred to herein as the "DNA-targeting RNA". A subject DNA-targeting RNA comprises two segments, a "DNA-targeting segment" and a "protein-binding segment." By "segment" it is meant a segment/section/region of a molecule, e.g., a contiguous stretch of nucleotides in an RNA. A segment can also mean a region/section of a complex such that a segment may comprise regions of more than one molecule. For example, in some cases the protein-binding segment (described below) of a DNA-targeting RNA is one RNA molecule and the protein-binding segment therefore comprises a region of that RNA molecule. In other cases, the protein-binding segment (described below) of a DNA-targeting RNA comprises two separate molecules that are hybridized along a region of complementarity. As an illustrative, non-limiting example, a protein-binding segment of a DNA-targeting RNA that comprises two separate molecules can comprise (i) base pairs 40-75 of a first RNA molecule that is 100 base pairs in length; and (ii) base pairs 10-25 of a second RNA molecule that is 50 base pairs in length. The definition of "segment," unless otherwise specifically defined in a particular context, is not limited to a specific number of total base pairs, is not limited to any particular number of base pairs from a given RNA molecule, is not limited to a particular number of separate molecules within a complex, and may include regions of RNA molecules that are of any total length and may or may not include regions with complementarity to other molecules.

The DNA-targeting segment (or "DNA-targeting sequence") comprises a nucleotide sequence that is complementary to a specific sequence within a target DNA (the complementary strand of the target DNA). The protein-binding segment (or "protein-binding sequence") interacts with a site-directed modifying polypeptide. When the site-directed modifying polypeptide is a Cas9 or Cas9 related polypeptide (described in more detail below), site-specific cleavage of the target DNA occurs at locations determined by both (i) base-pairing complementarity between the DNA-targeting RNA and the target DNA; and (ii) a short motif (referred to as the protospacer adjacent motif (PAM)) in the target DNA.

The protein-binding segment of a subject DNA-targeting RNA comprises two complementary stretches of nucleotides that hybridize to one another to form a double stranded RNA duplex (dsRNA duplex).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a Rad51 polypeptide" includes a plurality of such polypeptide and reference to "the Cas9 polypeptide" includes reference to one or more Cas9 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method for carrying out site-directed modification of a target DNA, the method comprising contacting the target DNA with: a) a complex comprising a Cas9 polypeptide and a guide RNA, wherein the guide RNA comprises a first segment comprising a nucleotide sequence that is complementary to a sequence in the target DNA and a second segment that binds to the Cas9 polypeptide; and b) a Rad51 polypeptide, wherein the Rad51 polypeptide enhances binding of the first segment to the target DNA.

A subject method for site-directed modification of a target DNA can be carried out in a living cell in vitro, in a living cell in vivo, or in a cell-free system in vitro.

Where a subject method for site-directed modification of a target DNA is carried out in a living cell, the cell can be an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, or a human cell.

A Cas9 polypeptide for use in a subject method can comprise an amino acid sequence having at least about 40%, at least about 45%, at least about 50%, at least about 55%, at least about 60%, at least about 65%, at least about 70%, at least about 75%, at least about 80%, at least about 85%, at least about 90%, at least about 95, at least about 98%, at least about 99%, or 100%, amino acid sequence identity to the amino acid sequence depicted in FIG. 23 (GenBank AAK33936). A Cas9 polypeptide for use in a subject method can comprise an amino acid sequence having at least about 40%, at least about 45%, at least about 50%, at least about 55%, at least about 60%, at least about 65%, at least about 70%, at least about 75%, at least about 80%, at least about 85%, at least about 90%, at least about 95, at least about 98%, at least about 99%, or 100%, amino acid sequence identity to an amino acid sequence described in Chylinski et al. (2013) *RNA Biol.* 10:726.

In some cases, different Cas9 polypeptides (i.e., Cas9 polypeptides from various species) may be advantageous to use in the various provided methods in order to capitalize on various enzymatic characteristics of the different Cas9 proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.). Cas9 proteins from various species of interest include, but are not limited to, those described in U.S. Patent Publication No. 2014/0068797 A1, the disclosure of which is incorporated herein by reference in its entirety.

In some embodiments, the site-directed modifying polypeptide comprises a modified form of the Cas9 polypeptide. In some instances, the modified form of the Cas9 polypeptide comprises an amino acid change (e.g., deletion, insertion, or substitution) that reduces the naturally-occurring nuclease activity of the Cas9 polypeptide. For example, in some instances, the modified form of the Cas9 polypeptide has less than 50%, less than 40%, less than 30%, less than 20%, less than 10%, less than 5%, or less than 1% of the nuclease activity of the corresponding wild-type Cas9 polypeptide. In some cases, the modified form of the Cas9 polypeptide has no substantial nuclease activity.

In some embodiments, the Cas9 polypeptide comprises a heterologous sequence (e.g., a fusion). In some embodiments, a heterologous sequence can provide for subcellular localization of Cas9 polypeptide (e.g., a nuclear localization signal (NLS) for targeting to the nucleus; a mitochondrial localization signal for targeting to the mitochondria; a chloroplast localization signal for targeting to a chloroplast; a ER retention signal; and the like). In some embodiments, a heterologous sequence can provide a tag for ease of tracking or purification (e.g., a fluorescent protein, e.g., green fluorescent protein (GFP), YFP, RFP, CFP, mCherry, tdTomato, and the like; a his tag, e.g., a 6×His tag; a hemagglutinin (HA) tag; a FLAG tag; a Myc tag; and the like). In some embodiments, the heterologous sequence can provide for increased or decreased stability.

In some embodiments, a subject Cas9 polypeptide can be codon-optimized. This type of optimization is known in the art and entails the mutation of foreign-derived DNA to mimic the codon preferences of the intended host organism or cell while encoding the same protein. Thus, the codons are changed, but the encoded protein remains unchanged. For example, if the intended target cell was a human cell, a human codon-optimized Cas9 (or variant, e.g., enzymatically inactive variant) would be a Cas9. Any suitable Cas9 polypeptide can be codon optimized. As another non-limiting example, if the intended host cell were a mouse cell, than a mouse codon-optimized Cas9 (or variant, e.g., enzymatically inactive variant) would be a suitable Cas9. While codon optimization is not required, it is acceptable and may be preferable in certain cases.

A Rad51 polypeptide for use in a subject method can comprise an amino acid sequence having at least about 70%, at least about 75%, at least about 80%, at least about 85%, at least about 90%, at least about 95, at least about 98%, at least about 99%, or 100%, amino acid sequence identity to the amino acid sequence depicted in FIG. 24 (GenBank CAG38796).

Rad51 polypeptides of interest also include, but are not limited to, those having an amino acid sequence of at least about 70%, at least about 75%, at least about 80%, at least about 85%, at least about 90%, at least about 95, at least about 98%, at least about 99%, or 100%, amino acid sequence identity to the amino acid sequence of UniProtKB accession numbers: Q0PWE1, R0KMM6, V5GKD1, P94102, O01679, Q2KJ94, M4SZA7, M4SMR0, G0NFX4, A8WXG6, G5EGG8, Q95Q25, L8E822, Q9XTK2, C1C0G1, U3E916, Q59UY8, Q8MKI8, W8CAP5, Q6Q242, J7G674, P70099, F2HIG6, Q6P5K8, Q27297, D7G6A4, R1DN08, R1C7C3, Q86C17, P37383, Q9NCP0, Q98SB7, L1J3X0, Q06609, Q9NZG9, E9PI54, E9PNT5, E9PJ30, H0YD61, T2MEE7, L7UU39, A4I3C9, O61127, C1BVX8, D3PGA1, Q0PWE6, Q0PWE4, Q0PWE9, Q0PWF3, Q0PWF2, Q0PWF6, Q0PWF7, Q0PWF5, Q0PWF4, Q0PWF1, Q0PWE7, Q0PWE5, Q0PWE8, Q0PWF0, Q0PWE3, Q0PWE2, F7GCI3, L7UQJ6, Q08297, A3KGI2, F7AT35, D6RCK1, U6D555, R0LZJ3, R0MEL7, O77507, G1TCL3, H2Q966, B7G0B3, B7FT85, Q7Z9J0, Q8IIS8, A3E3X4, A3E3X6, B5DF04, I2FLH5, P25454, P36601, Q40134, F7W1D5, E7A2J0, B0M1M6, O76341, M5BI63, I6XGP4, B5LW22, B9VR65, B9VR66, Q9U6W1, Q99133, Q91918, and Q91917.

The Rad51 polypeptide can increase hybridization of the first segment of the guide RNA to the target DNA by at least about 10%, at least about 20%, at least about 25%, at least about 50%, at least about 75%, at least about 2-fold, at least about 2.5-fold, at least about 5-fold, at least about 10-fold, at least about 25-fold, at least about 50-fold, at least about 100-fold, or more than 100-fold, compared to the hybridization of the first segment of the guide RNA to the target DNA in the absence of the Rad51 polypeptide.

In a subject method, in some embodiments, the Cas9 polypeptide introduces a single-strand or double-strand break in the target DNA. In some cases, modification of the target DNA comprises replacement of all or a portion of the target DNA with a heterologous DNA.

In a subject method, in some embodiments, the Rad51 polypeptide is heterologous to the cell. In some cases, where a subject method is carried out in a living cell, the cell has been genetically modified with a heterologous nucleic acid that comprises a nucleotide sequence encoding the Rad51 polypeptide. For example, the Rad51 polypeptide can be encoded on a recombinant expression vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544). In some cases, genetic modification with a heterologous nucleic acid that comprises a nucleotide sequence encoding a Rad51 polypeptide provides for a level of Rad51 that is at least 10% higher than the level of Rad51 polypeptide in a control cell not genetically modified with a heterologous nucleic acid that comprises a nucleotide sequence encoding the Rad51 polypeptide.

In a subject method, in some embodiments, where a subject method is carried out in a living cell, the cell has been genetically modified with a heterologous nucleic acid that comprises a nucleotide sequence encoding the Cas9 polypeptide. For example, the Cas9 polypeptide can be encoded on a recombinant expression vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some cases, the Cas9 polypeptide and the Rad51 polypeptide are encoded on the same expression vector.

Guide RNAs suitable for use in a subject method include a portion (segment) that hybridizes to a target DNA of interest. The segment that hybridizes to a target DNA of interest can be readily designed by those skilled in the art, given the nucleotide sequence of the target DNA. The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

Guide RNAs suitable for use in a subject method include a segment that binds to the Cas9 polypeptide. Sequences of the segment that bind to a Cas9 polypeptide are known in the art. See, e.g., Chylinski et al. (2013) *RNA Biol.* 10:726; Jinek et al. (2012) *Science* 337:816; Mali et al. (2013) *Science* 339:823; and Cong et al. (2013) *Science* 339:819. The Cas9-binding segment can have a length of from about 12 nucleotides to about 100 nucleotides. For example, the Cas9-binding segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the Cas9-binding segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

In certain embodiments, the component sequences of the guide RNA may be joined by intervening nucleotides ("linkers" or "linker nucleotides") that may make up one or more linker segments. Linkers that find use in methods of the present disclosure can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt.

A guide RNA and a Cas9 polypeptide (i.e., site-directed polypeptide) form a complex (i.e., bind via non-covalent interactions). The guide RNA provides target specificity to the complex by comprising a nucleotide sequence that is complementary to a sequence of a target DNA. The Cas9 polypeptide of the complex provides the site-specific activity. In other words, the Cas9 polypeptide is guided to a target DNA sequence (e.g. a target sequence in a chromosomal nucleic acid; a target sequence in an extrachromosomal nucleic acid, e.g. an episomal nucleic acid, a minicircle, etc.; a target sequence in a mitochondrial nucleic acid; a target sequence in a chloroplast nucleic acid; a target sequence in a plasmid; etc.) by virtue of its association with the protein-binding segment of the guide RNA.

Genetically Modified Host Cells

The present disclosure provides an isolated genetically modified host cell, where the genetically modified host cell is genetically modified with one or more nucleic acids comprising nucleotide sequences encoding a Cas9 polypeptide and a Rad51 polypeptide. In some embodiments, the host cell is also genetically modified with a nucleic acid comprising a nucleotide sequence encoding a guide RNA.

Transgenic Non-Human Organism

A transgenic non-human organism whose genome comprises: a) a transgene comprising a nucleotide sequence encoding a Cas9 polypeptide; and b) a transgene comprising a nucleotide sequence encoding a Rad51 polypeptide.

A subject transgenic non-human organism can be an animal. In some embodiments, the transgenic non-human animal is homozygous for the genetic modification. In some embodiments, the transgenic non-human animal is heterozygous for the genetic modification. In some embodiments, the transgenic non-human animal is a vertebrate, for example, a fish (e.g., zebra fish, gold fish, puffer fish, cave fish, etc.), an amphibian (frog, salamander, etc.), a bird (e.g., chicken, turkey, etc.), a reptile (e.g., snake, lizard, etc.), a mammal (e.g., an ungulate, e.g., a pig, a cow, a goat, a sheep, etc.; a lagomorph (e.g., a rabbit); a rodent (e.g., a rat, a mouse); a non-human primate; etc.), etc.

The transgene (Cas9 transgene; Rad51 transgene) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

A subject transgenic organism can be a plant. The plant can be heterozygous or homozygous for the transgenes.

Kits

The present disclosure provides a kit for carrying out a subject method. A subject kit can include: a) a Cas9 polypeptide; b) a guide RNA; and c) a Rad51 polypeptide. A subject kit can further include one or more additional reagents for carrying out site-directed modification of a target DNA. Examples of such additional reagents include: a dilution buffer; a reconstitution solution; a wash buffer; a control reagent.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

*Saccharomyces cerevisiae* was used as a model system to test in vivo the role of Rad51p in hybrid formation. It is reported that the formation of RNA-DNA hybrids and associated genome instability in at least four RNA biogenesis mutants requires Rad51p and it activator, Rad52p. Furthermore, the deleterious hybrid-forming activity of Rad51p is suppressed in wild-type cells by Srs2p, a Rad51p inhibitor. Additionally, a model locus system was developed that allows us to monitor hybrid-mediated genome instability as a result of transcription. This system was manipulated to provide compelling evidence that hybrids and ensuing genome instability can occur via a trans mechanism that is dependent on Rad51p.

Materials and Methods

Yeast Strains, Media and Reagents

Full genotypes for the strains used in this study are listed in Table 1 provided below. Strain LW6811, the YAC-GALpr strain was made by integrating the GAL1-10 promoter, along with the selectable marker CLONAT at site 323,280 kb on the YAC. The trans YAC module, in LW7003 encompasses 1 kb of the YAC, along with the GALpr and CLONAT marker integrated on chromosome III in place of the BUDS (YCR038C) Open Reading Frame. All integrations were done using standard one-step PCR techniques. The 70mers used for integration are listed in Table 2 provided in FIG. 25. The empty control and RNAse H plasmids used are 2μ plasmids, previously described in Wahba et al., 2011. Yeast strains were grown in YEP or minimal media supplemented with 2% glucose. 5-Fluoroorotic (5-FOA) was purchased from Bio Vectra.

TABLE 1

| Strain | Strain number | Genotype |
|---|---|---|
| | | YAC single deletion strains |
| wt YAC | LW 6732c | MATa his3Δ ura3Δ0 met15Δ0 leu2Δ0/YAC (MFA1pr-HIS3 URA3 MET15 TRP1) |
| leo1Δ-YAC | LW5008a | MATa leo1Δ:KANAMYCIN his3Δ ura3Δ0 met15Δ0 leu2Δ0/YAC (MFA1pr-HIS3 URA3 MET15 TRP1) |
| sin3Δ-YAC | LW5067a | MATa sin3Δ:KANAMYCIN his3Δ ura3Δ0 met15Δ0 leu2Δ0/YAC (MFA1pr-HIS3 URA3 MET15 TRP1) |
| med12Δ-YAC | LW5012a | MATa med13Δ:KANAMYCIN his3Δ ura3Δ0 met15Δ0 leu2Δ:CLONAT/YAC (MFA1pr-HIS3 URA3 MET15 TRP1) |
| kem1Δ-YAC | MV14 | MATa kem1Δ:KANAMYCIN his3Δ ura3Δ0 met15Δ0 leu2Δ:CLONAT/YAC (MFA1pr-HIS3 URA3 MET15 TRP1) |
| rrp6Δ-YAC | LW6736a | MATa rrp6Δ:KANAMYCIN his3Δ ura3Δ0 met15Δ0 leu2Δ0/YAC (MFA1pr-HIS3 URA3 MET15 TRP1) |
| rad51Δ-YAC | LW6733a | MATa kem1Δ:KANAMYCIN his3Δ ura3Δ0 met15Δ0 leu2Δ:CLONAT/YAC (MFA1pr-HIS3 URA3 MET15 TRP1) |
| rad52Δ-YAC | LW5096 | MATa rad52Δ:KANAMYCIN his3Δ200 ura3Δ0 met15Δ0 leu2Δ0/YAC (MFA1pr-HIS3 URA3 MET15 TRP1) |
| srs2Δ-YAC | LW6742b | MATa srs2Δ:KANAMYCIN his3Δ ura3Δ0 met15Δ0 leu2Δ:CLONAT/YAC (MFA1pr-HIS3 URA3 MET15 TRP1) |
| rad54Δ-YAC | LW6743a | MATa rad54Δ:CLONAT his3Δ200 ura3Δ0 met15Δ0 leu2Δ0/YAC (MFA1pr-HIS3 URA3 MET15 TRP1) |
| rdh54Δ-YAC | LW6744a | MATa rdh54Δ:KANAMYCIN his3Δ ura3Δ0 met15Δ0 leu2Δ:CLONAT/YAC (MFA1pr-HIS3 URA3 MET15 TRP1) |
| rad54Δrdh54Δ-YAC | LW6746 | MATa rdh54Δ:KANAMYCIN rad54Δ:CLONAT his3Δ200 ura3Δ0 met15Δ0 leu2Δ0/YAC (MFA1pr-HIS3 URA3 MET15 TRP1) |
| | | YAC double/triple deletion strains |
| leo1Δrad51Δ-YAC | LW6747a | MATa leo1Δ:KANAMYCIN rad51Δ:HYGROMYCIN B his3Δ ura3Δ0 met15Δ0 leu2Δ0/YAC (MFA1pr-HIS3 URA3 MET15 TRP1) |
| sin3Δrad51Δ-YAC | LW6730a | MATa sin3Δ:KANAMYCIN rad51Δ:CLONAT his3Δ ura3Δ0 met15Δ0 leu2Δ0/YAC (MFA1pr-HIS3 URA3 MET15 TRP1) |
| med12Δrad51Δ-YAC | LW6751a | MATa med12Δ:KANAMYCIN rad51Δ:CLONAT his3Δ ura3Δ0 met15Δ0 leu2Δ0/YAC (MFA1pr-HIS3 URA3 MET15 TRP1) |
| kem1Δrad51Δ-YAC | LW6750a | MATa kem1Δ:KANAMYCIN rad51Δ:HYGROMYCIN B his3Δ ura3Δ0 met15Δ0 leu2Δ:CLONAT/YAC (MFA1pr-HIS3 URA3 MET15 TRP1) |
| rrp6Δrad51Δ-YAC | LW6749a | MATa rrp6Δ:KANAMYCIN rad51Δ:HYGROMYCIN B his3Δ ura3Δ0 met15Δ0 leu2Δ0/YAC (MFA1pr-HIS3 URA3 MET15 TRP1) |
| srs2Δrad51Δ-YAC | LW6763 | MATa srs2Δ:KANAMYCIN rad51Δ:CLONAT his3Δ ura3Δ0 met15Δ0 leu2Δ:CLONAT/YAC (MFA1pr-HIS3 URA3 MET15 TRP1) |

TABLE 1-continued

| Strain | Strain number | Genotype |
|---|---|---|
| leo1Δrad52Δ-YAC | LW6755a | MATa leo1Δ:KANAMYCIN rad52Δ:HYGROMYCIN B his3Δ ura3Δ0 met15Δ0 leu2Δ0/YAC (MFA1pr-HIS3 URA3 MET15 TRP1) |
| sin3Δrad52Δ-YAC | LW6761a | MATa sin3Δ:KANAMYCIN rad52Δ:HYGROMYCIN B his3Δ ura3Δ0 met15Δ0 leu2Δ0/YAC (MFA1pr-HIS3 URA3 MET15 TRP1) |
| med12Δrad52Δ-YAC | LW6752a | MATa med12Δ:KANAMYCIN rad52Δ:HYGROMYCIN B his3Δ ura3Δ0 met15Δ0 leu2Δ0/YAC (MFA1pr-HIS3 URA3 MET15 TRP1) |
| kem1Δrad52Δ-YAC | LW6756 | MATa kem1Δ:KANAMYCIN rad52Δ:HYGROMYCIN B his3Δ ura3Δ0 met15Δ0 leu2Δ:CLONAT/YAC (MFA1pr-HIS3 URA3 MET15 TRP1) |
| rrp6Δrad52Δ-YAC | LW6753a | MATa rrpΔ4:KANAMYCIN rad52Δ:HYGROMYCIN B his3Δ ura3Δ0 met15Δ0 leu2Δ0/YAC (MFA1pr-HIS3 URA3 MET15 TRP1) |
| rnh1Δrnh201Δ-YAC | LW5083 | MATa rnh1Δ:HYGROMYCIN rnh201Δ:CLONAT his3Δ ura3Δ0 met15Δ0 leu2Δ/YAC (MFA1pr-HIS3 URA3 MET15 TRP1) |
| rnh1Δrnh201Δ rad52Δ-YAC | LW6766a | MATa rnh1Δ:HYGROMYCIN rnh201Δ:CLONAT rad52Δ:KANAMYCIN his3Δ ura3Δ0 met15Δ0 leu2Δ/YAC (MFA1pr-HIS3 URA3 MET15 TRP1) |
| rnh1Δrnh201Δ rad51Δ-YAC | LW6771a | MATa rnh1Δ:KANAMYCIN rnh201Δ:CLONAT rad51Δ:HYGROMYCIN B his3Δ ura3Δ0 met15Δ0 leu2Δ/YAC (MFA1pr-HIS3 URA3 MET15 TRP1) |
| | | rDNA instability strains |
| wt | 3003-RKY1145 | MATa his4Δ ura3Δ lys2Δ leu2Δ hoΔ::LYS2 25SRNA::URA3 |
| srs2Δ | LW6810a | MATa srs2Δ:HYGROMYCIN his4Δ ura3Δ lys2Δ leu2Δ hoΔ::LYS2 25SRNA::URA3 |
| | | Cis/trans strains |
| YAC pGAL | LW6811a | MATa his3Δ ura3Δ0 met15Δ0 leu2Δ0/YAC (MFA1pr-HIS3 URA3 MET15 TRP1 CLONAT-pGAL1-10) |
| YAC pGAL, rad51Δ | LW6830a | MATa rad51Δ::KANAMYCIN his3Δ ura3Δ0 met15Δ0 leu2Δ0/YAC (MFA1pr-HIS3 URA3 MET15 TRP1 CLONAT-pGAL1-10) |
| YAC trans pGAL | LW7003a | MATa his3Δ ura3Δ0 met15Δ0 leu2Δ0 bud5Δ::CLONAT-pGAL1-10-YACseq/YAC (MFA1pr-HIS3 URA3 MET15 TRP1) |
| YAC trans pGAL, rad51Δ | LW7004a | MATa rad51Δ::KANAMYCIN his3Δ ura3Δ0 met15Δ0 leu2Δ0 bud5Δ::CLONAT-pGAL1-10-YACseq/YAC (MFA1pr-HIS3 URA3 MET15 TRP1) |
| | | HA-tagged RAD51 strains |
| inducible Chr III HO cut site | MH3579 | Δho Δhml1:ADE1 Δhmr::ADE1 ade1-110 leu2,3-112 lys5 trp1::hisG ura3-52 ade3::GAL10:HO RAD51-3xV5(KAN) |
| YAC, RAD51-3xHA | LW6790 | MATa RAD51-3xHA(KAN) his3Δ ura3Δ0 met15Δ0 leu2Δ0/YAC (MFA1pr-HIS3 URA3 MET15 TRP1) |
| YAC pGAL, RAD51-3xHA | LW6794a | MATa RAD51-3xHA(KAN) his3Δ ura3Δ0 met15Δ0 leu2Δ0/YAC (MFA1pr-HIS3 URA3 MET15 TRP1 CLONAT-pGAL1-10) |

Quantitative Assay for YAC Instability

Cells were dilution streaked out on SC-URA plates to select for the YAC terminal marker (URA3). Single colonies were then picked and resuspended in 0.5 mL of water, diluted, and $10^5$ cells were plated onto 5-FOA and -HIS (5-FOA) plates. Plating efficiency was monitored by plating 200 cells onto rich media plates. Plates were incubated at 30° C. 3 days after which the number of colonies formed on each plate was counted. The number of colonies that grow on 5-FOA, normalized for plating efficiencies is a measure of the rate of events.

Chromosome Spreads and Microscopy

Chromosome spreads were performed as previously described (Wahba et al., 2011). Slides were incubated with the mouse monoclonal antibody S9.6 directed to RNA-DNA hybrids, and available in the hybridoma cell line HB-8730. The primary antibody was diluted 1:2000 in blocking buffer (5% BSA, 0.2% Milk, 1×PBS) for a final concentration 0.25 ug/mL. The secondary Cy3-conjugated goat anti-mouse antibody was obtained from Jackson labs (#115-165-003) and diluted 1:2000 in blocking buffer. Indirect immunofluorescence (IF) was observed using an Olympus IX-70 microscope with a 100×/NA 1.4 objective, and Orca II camera (Hamamatsu, Bridgewater, N.J.).

Liquid Assay for YAC Instability with Galactose Induction

Cells were picked from SC-URA plates, resuspended in SC-URA media, and grown to saturation. Fresh YEP or -URA media with 2% lactic acid, 3% glycerol was inoculated to a O.D. of ~0.3, and allowed to double to an O.D. of ~1.0. Galactose was then added to a final concentration of 2%. Cells were shaken at 30° C. and then plated onto 5-FOA 0, 2 and 5 hours post induction with galactose. Plating efficiency was monitored by plating 200 cells onto rich media plates.

Dot Blotting with S9.6 Antibody

Genomic DNA was isolated using the Qiagen Genomic DNA kit. Roughly 1 µg of DNA was resuspended to a final volume of 50 µl in nuclease-free water, and spotted directly on to a nylon GeneScreen Plus membrane (Perkin Elmer NEF988) using a Bio-Dot Microfiltration Apparatus (Bio-Rad). The membrane was UV-crosslinked and blocked with 5% 1×PBS/0.1% Tween-20 prior to incubation with primary and secondary antibodies. 5 µg of S9.6 antibody was used for the primary, and a 25,000× dilution of goat anti-mouse HRP (BioRad) was used as the secondary. HRP signal was developed with Clarity Western ECL Substrate (BioRad), and exposed to autoradiography film.

Quantitative Reverse Transcriptase PCR

Total RNA was isolated using an RNeasy Mini Kit (Qiagen®). Reverse Transcriptase was done with specified primer pairs using the OneStep RT-PCR Kit (Qiagen), and quantified using SYBR Green and the DNA Engine Opticon® Continuous Fluorescence Detection System.

DNA Immunoprecipitation (DIP)

DIP analysis was performed as previously described (Alzu et al., 2012; Mischo et al., 2011b). Briefly, 150 to 200 µg of genomic DNA isolated using the Qiagen Genomic DNA kit was sonicated, precipitated and resuspended in 50

μl of nuclease-free water. 350 μl of FA buffer (1% Triton x-100, 0.1% sodium deoxycholate, 0.1% SDS, 50 mM HEPES, 150 mM NaCl, 1 mM EDTA) was then added to the DNA, and incubated for 90 minutes with 5 μg of S9.6 antibody prebound to magnetic protein A beads. Beads were then washed and the DNA eluted according to standard Chromatin immunoprecipitation protocols. % RNA-DNA hybrid amounts were quantified using quantitative PCRs on DNA samples from DIP and total DNA with DyNAmo HS SYBR green qPCR kit (Thermo).

Chromatin Immunoprecipitation

Cells used for chromatin immunoprecipitation experiments were grown in YEP media with 2% lactic acid, 3% glycerol and collected either before adding galactose (−Gal), or 2 hours post addition of galactose at a final 2% concentration (+Gal). Standard Chromatin immunoprecipitation was performed as described previously (Unal et al., 2004). Briefly, $5 \times 10^8$ cells were crosslinked in 1% formaldehyde for 30 minutes at room temperature. Chromatin was sheared 20 times for 45 seconds each (settings at Duty Cycle: 20%, Intensity: 10, Cycles/Burst: 200), with 30 seconds of rest in between using a Covaris S2. Immunoprecipitation of Rad51-HA or untagged Rad51p was done with anti-HA antibody (Roche) or anti-Rad51p polyclonal antibody (Santa Cruz). Immunoprecipitation of γ-H2a.X was done with anti-γ-H2a.X (Abcam). A no primary antibody control is also run to ensure specificity. Appropriate dilutions of input and immunoprecipitated DNA samples were used for PCR analysis to ensure linearity of the PCR signal. PCR and data analysis was done as described (Unal et al., 2004). With the exception of the experiment in FIG. 15 which was done once, all experiments were done at least twice and a representative data set is shown. ChIP primers are listed in Table 2 provided in FIG. 25.

Pulse-Field Gel Electrophoresis and Southern Analysis

Yeast genomic DNA was prepared in 1% pulse-field grade agarose plugs (SeaPlaque 50100) and resolved as previously described (Schwartz and Cantor, 1984) with a Bio-Rad CHEF-DR III system. The following parameters were used: 6 V/cm, 120° angle, 20-50 s switch times, 17 hours at 14° C. For southern analysis, gels were transferred onto a GeneScreen Plus membrane (Perkin Elmer NEF988) and probed with a 0.5 kb fragment containing HISS sequence.

Quantitative Assay for rDNA Instability

Cells were dilution streaked out on SC-URA. The rate of rDNA instability was calculated from 5-FOA plates as described above for YAC instability.

Results

Formation of RNA-DNA Hybrids is Dependent on Rad51p

The conditions that drive the initial formation of RNA-DNA hybrids in vivo are not well understood. With the bacterial in vitro experiments in mind, we wondered whether hybrid formation was simply a strand exchange reaction, similar to that mediated by Rad51p during DNA repair and homologous recombination. To test this possibility, we examined the effect of deleting RAD51 on hybrid formation, and the associated genome instability in RNA biogenesis mutants of budding yeast. We chose a representative set of mutants defective in elongation (leo1Δ), repression (med12Δ and sin3Δ) and degradation (kem1Δ and rrp6Δ). We assayed directly for the presence of RNA-DNA hybrids in wild type and these mutants by staining chromosomes in spread nuclei with S9.6 antibody (see Methods). Previously, we demonstrated the specificity of the S9.6 antibody for hybrids by two approaches. First, S9.6 staining in spreads of RNA biogenesis mutants is reduced to that seen in WT by post treatment of chromosome spreads with RNase H (Wahba et al., 2011). Similarly spreads of an RNA biogenesis mutant over-expressing RNase H no longer stained with S9.6.

Figure 10:
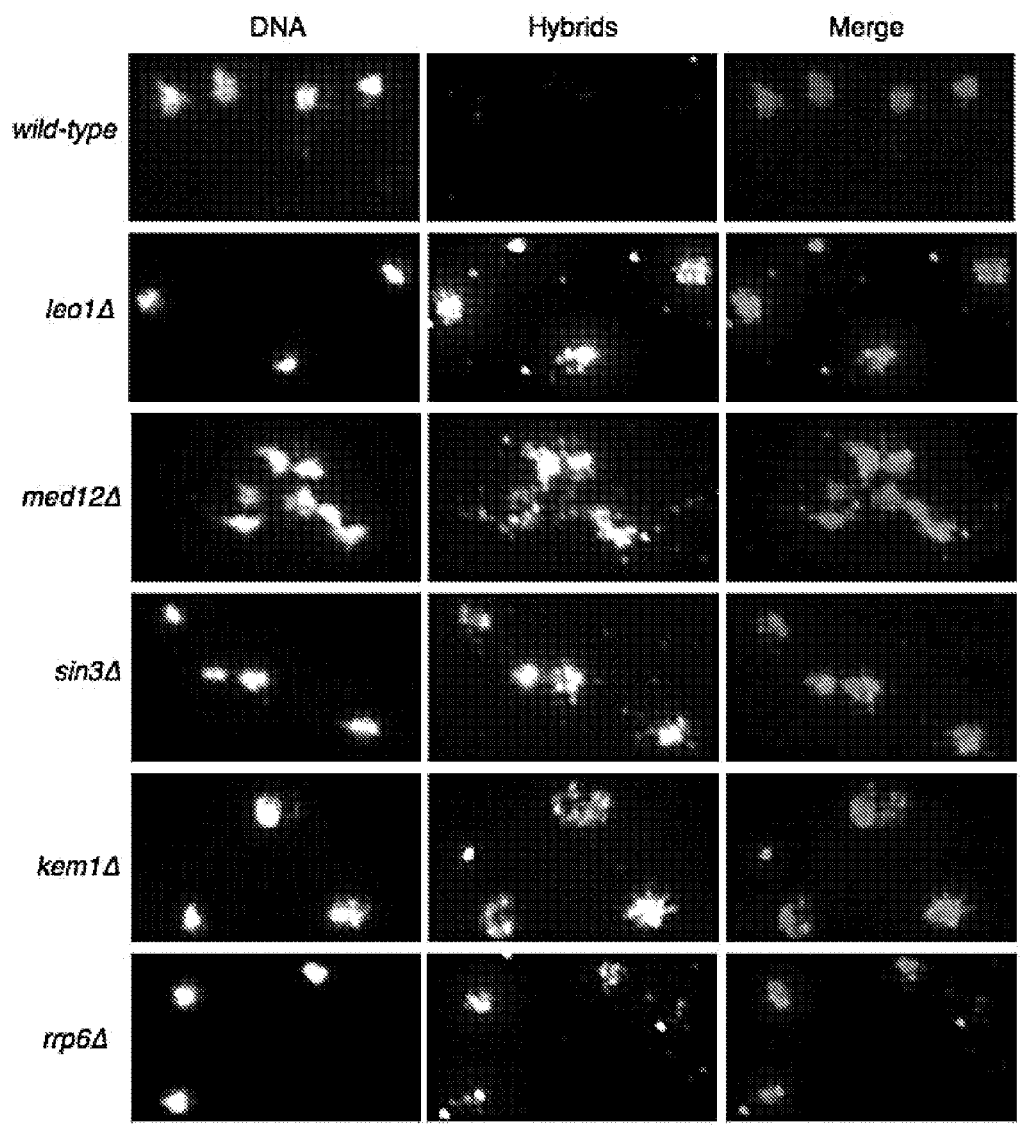
FIG. 10. Larger panels of chromatin spreads showing multiple nuclei of single mutants stained with S9.6 antibody.
Figure 11:
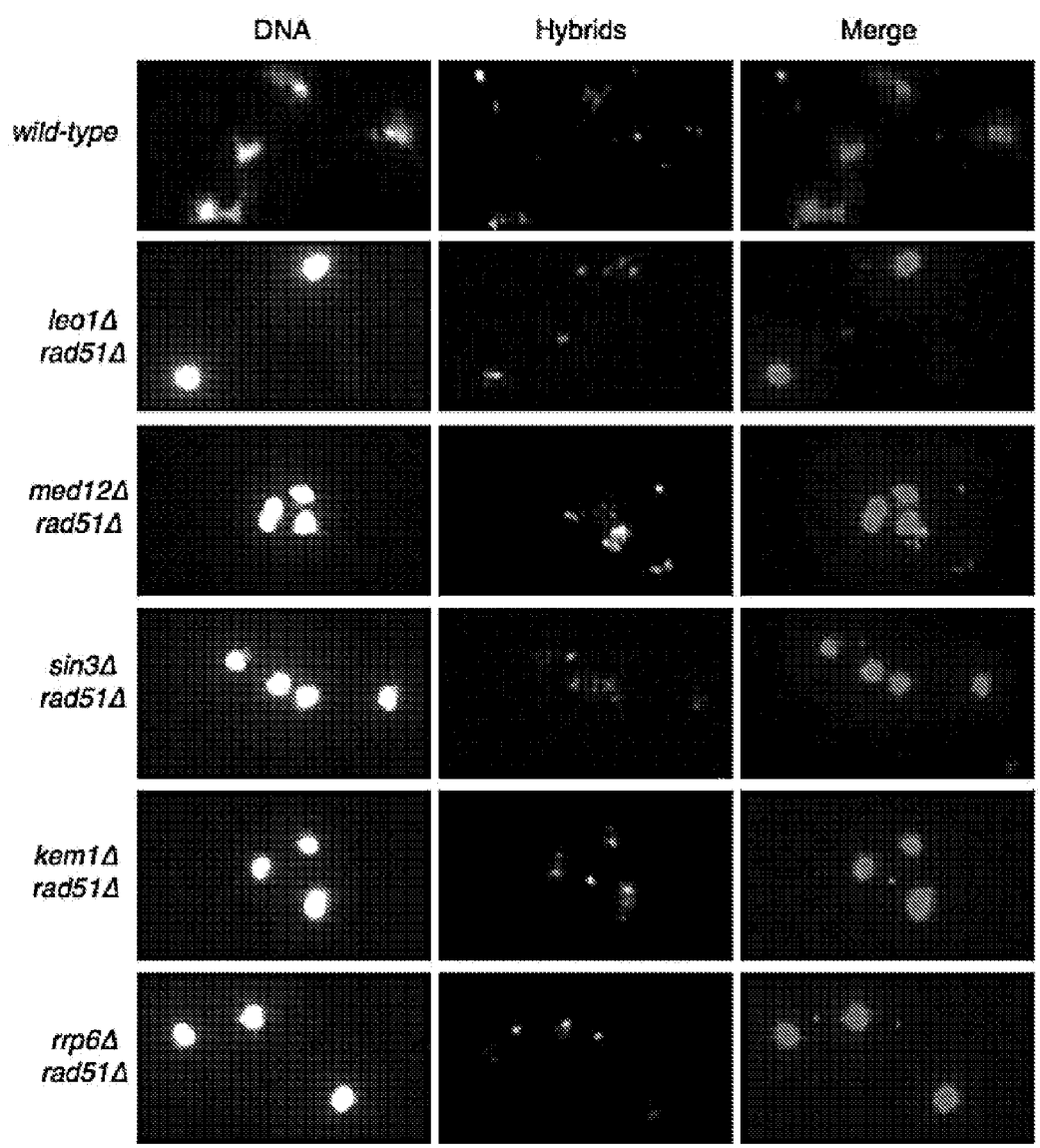
FIG. 11. Larger panels of chromatin spreads showing multiple nuclei of double mutants stained with S9.6 antibody.
Figure 12:
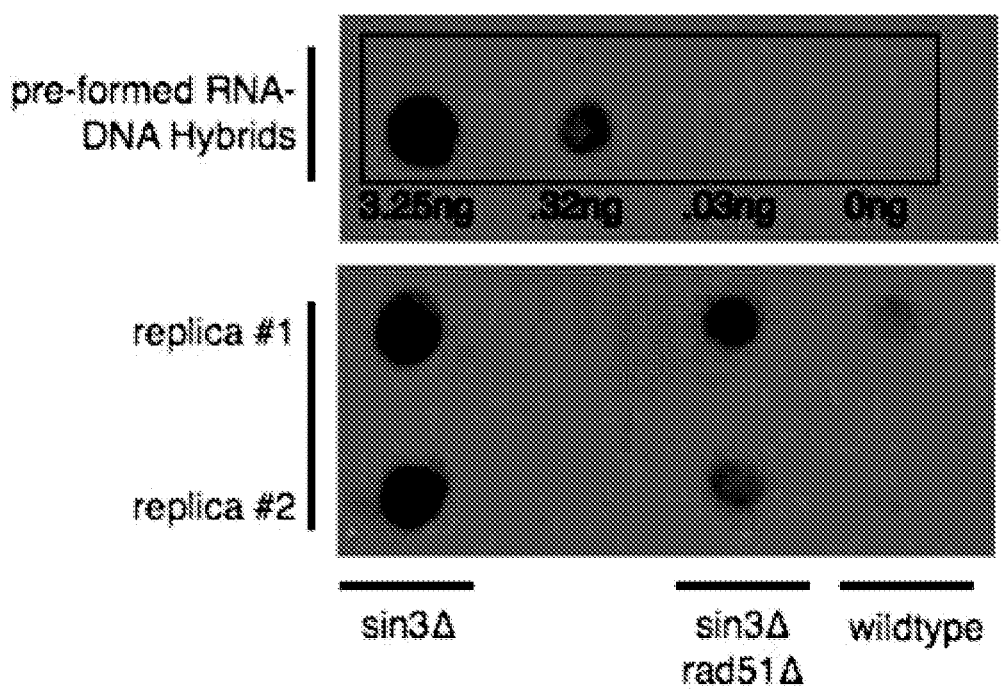
FIG. 12. Dot blotting with S9.6 antibody.

As reported previously, less than 5% of wild-type nuclei stain with this antibody (FIG. 1a, FIG. 10). In contrast, 80-85% of nuclei in the representative set of RNA biogenesis mutants showed robust staining, indicating the formation of stable hybrids at many loci in most cells (FIG. 1a, FIG. 10). The deletion of RAD51 (rad51Δ) in these mutants diminished S9.6 staining in nearly all nuclei from the RNA biogenesis mutants 3- to 4-fold to near background level (FIG. 1a, FIG. 11). To corroborate the cytological method, total nucleic acids were isolated from wild-type, sin3Δ (a representative RNA biogenesis mutant) and sin3Δ rad51Δ cells, transferred to a solid matrix and binding of S9.6 was monitored. S9.6 binding to sin3Δ nucleic acids was elevated approximately 10 fold relative to sin3Δ rad51Δ (FIG. 12). These results show that hybrid formation in these mutants is highly dependent upon Rad51p.

One prediction from the cytological results is that the suppression of hybrid formation by rad51Δ should also lead to a suppression of hybrid-mediated chromosome instability. To measure hybrid-mediated genome instability, we exploited an assay developed previously using a yeast artificial chromosome (YAC) ((Wahba et al., 2011), See Methods). The total rate of YAC instability (the sum of chromosome loss and terminal deletions) in wild-type cells was $6 \times 10^{-4}$ per division. Notably, rad51Δ alone caused no increase in YAC instability. In our subset of RNA biogenesis mutants YAC instability increased 5 to 10 fold (FIG. 1b). The introduction of the rad51Δ into the RNA biogenesis mutants completely suppressed the elevated YAC instability, both chromosome loss and terminal deletions, in leo1Δ, kem1Δ, rrp6Δ and sin3Δ mutants. In the med12Δ, YAC instability was mostly but not entirely suppressed despite the near complete suppression of hybrid formation as monitored by spreads, indicating that in the med12Δ rad51Δ strain a subset of the YAC instability was hybrid independent. Overall, the suppression of hybrid-mediated chromosome instability by rad51Δ corroborates its elimination of RNA-DNA hybrids and associated destabilizing lesions.

To further validate the occurrence of Rad51-dependent hybrids, a model locus was developed that can be used to induce hybrid formation and hybrid-mediated instability at a known region. From previous study on RNA biogenesis mutants that induce hybrids, it was noted that many of these mutants allow cryptic transcription, and likely the production of aberrant transcripts (Cheung et al., 2008; Wahba et al., 2011; Wyers et al., 2005). Based on this observation, a portion of the GAL1-10 promoter was introduced into the YAC (henceforth referred to as YAC-GALpr), such that the addition of galactose to the media would induce GALpr-dependent transcription of neighboring non-yeast sequences (FIG. 2a). We analyzed transcription of the human and vector sequences flanking GALpr by qRT-PCR. This analysis revealed approximately 100-fold induction of RNA at least 1 Kb on both sides of the GAL promoter (FIG. 2b).

Using the model locus, we monitored the presence of transcription-induced hybrids specifically proximal to GALpr. Total nucleic acids were isolated from strains containing either the YAC or YAC-GALpr in the presence or absence of galactose. These samples were subjected to DNA immunoprecipitation (DIP) analysis with the S9.6 antibody that should only precipitate DNA in RNA-DNA hybrids ((Mischo et al., 2011b), Methods). Using primers specific to the YAC region proximal to the GALpr, low DIP signals were observed in YAC-GALpr cultures in the absence of galactose, as well as in cultures with the YAC, with and without addition of galactose (FIG. 2c, FIG. 13A). Thus, hybrids form rarely in the YAC sequences proximal to the GALpr in the absence of their transcription. In contrast, a dramatic increase in the DIP signal for hybrids on the YAC sequences proximal to YAC-GALpr, two hours after induction by galactose was observed (FIG. 2c). The specificity of this increased DIP signal was evident by the fact that no elevation in hybrid signal was detected in two regions of the YAC-GALpr distal to the GALpr (FIG. 13B). Additionally, lower DIP signals coincide with the transcriptional start site of the GALpr, where there is little transcript detectable upon addition of galactose (FIG. 2c). Furthermore, the DIP signal in the YAC-GALpr strains was suppressed when transcription was repressed by the addition of glucose (FIG. 13C). Finally, hybrid formation at YAC-GALpr was dependent upon RAD51 (see below). These data provide molecular evidence for the formation of RAD51-dependent hybrids at the YAC sequences transcribed by induction of GALpr.

Figure 2:
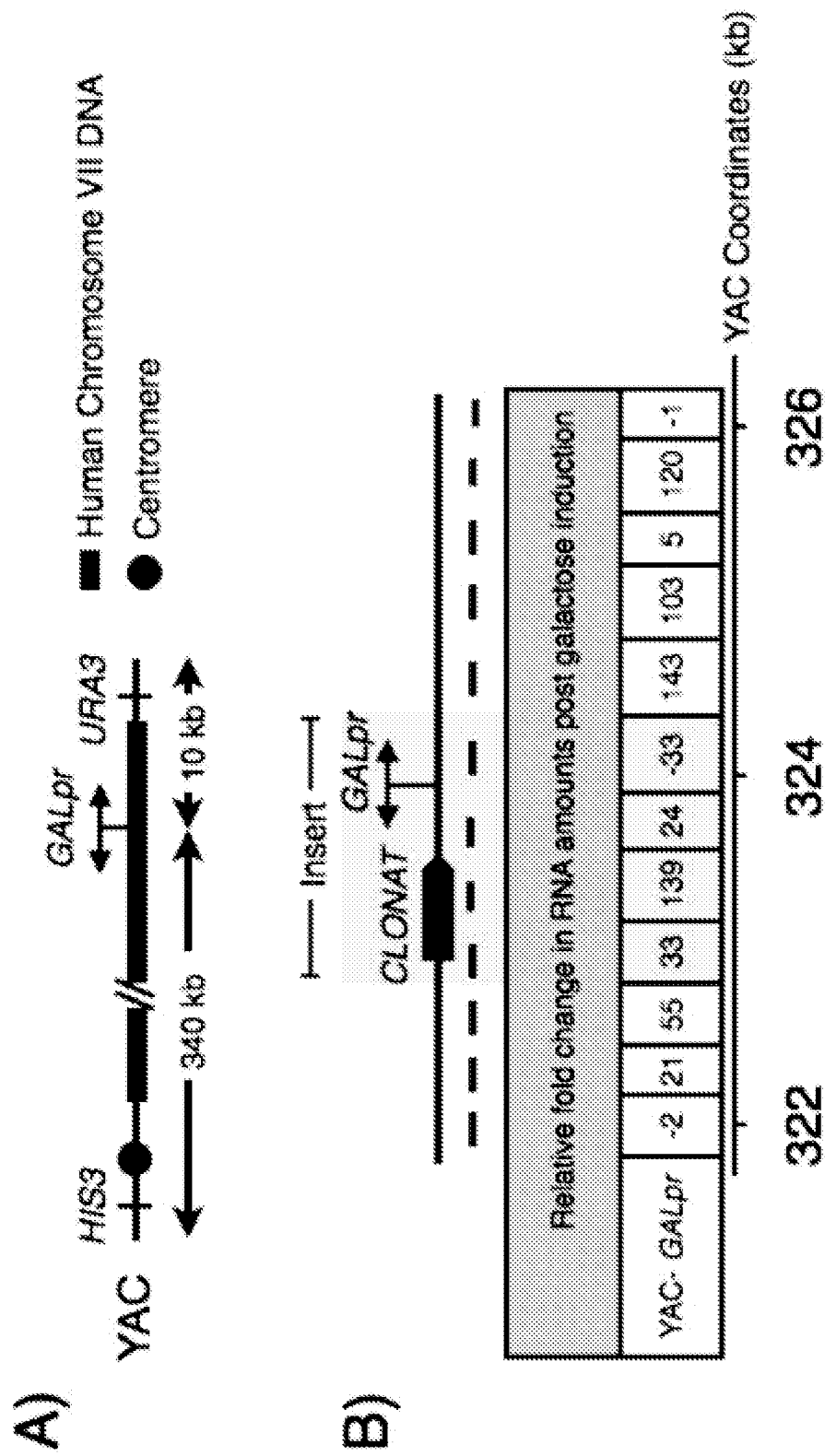
FIG. 2. Hybrid-mediated YAC instability is induced in wild-type when high rates of transcription are induced on the YAC using the GAL1-10 promoter (GALpr).
Figure 2:
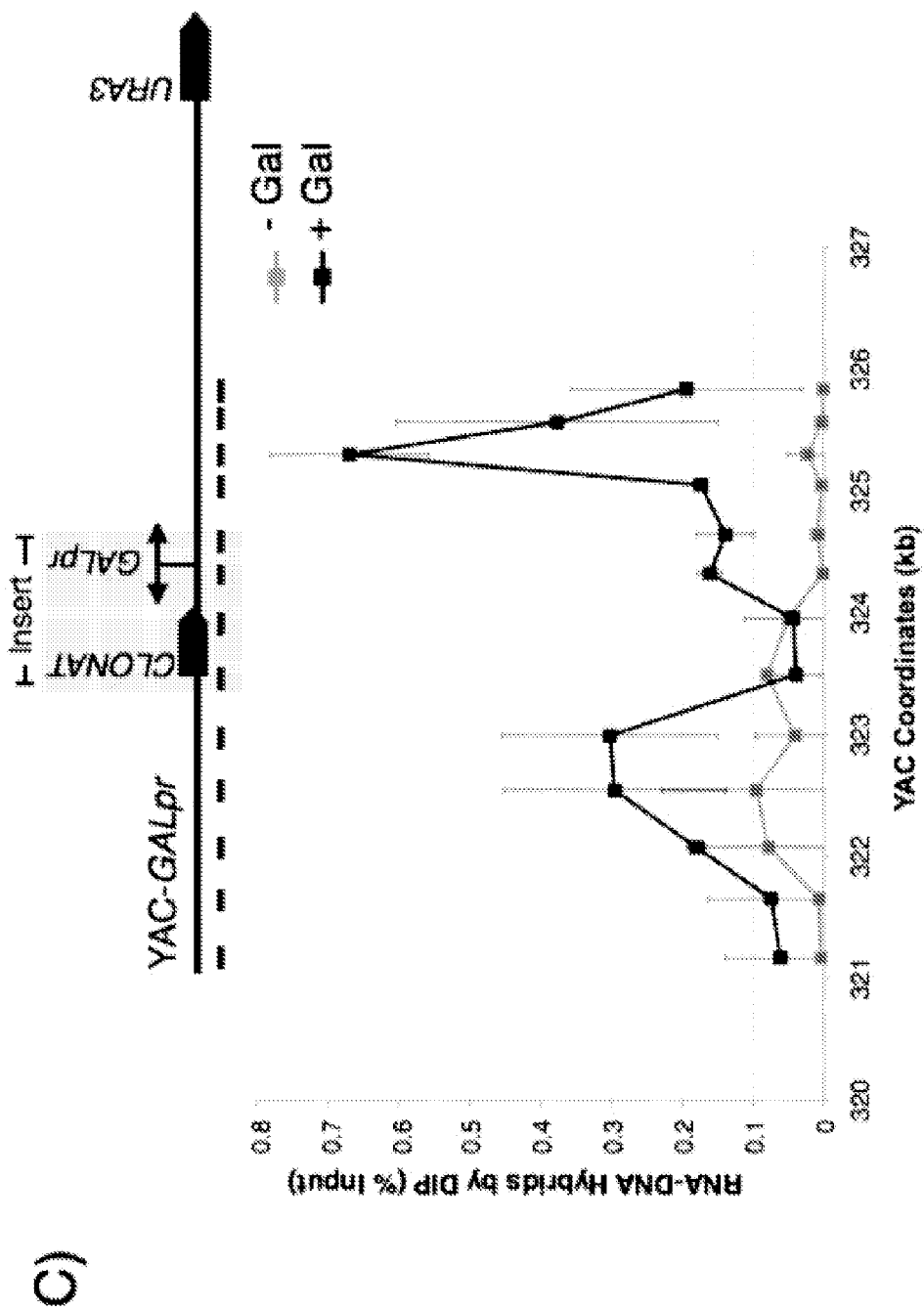
Figure 14:
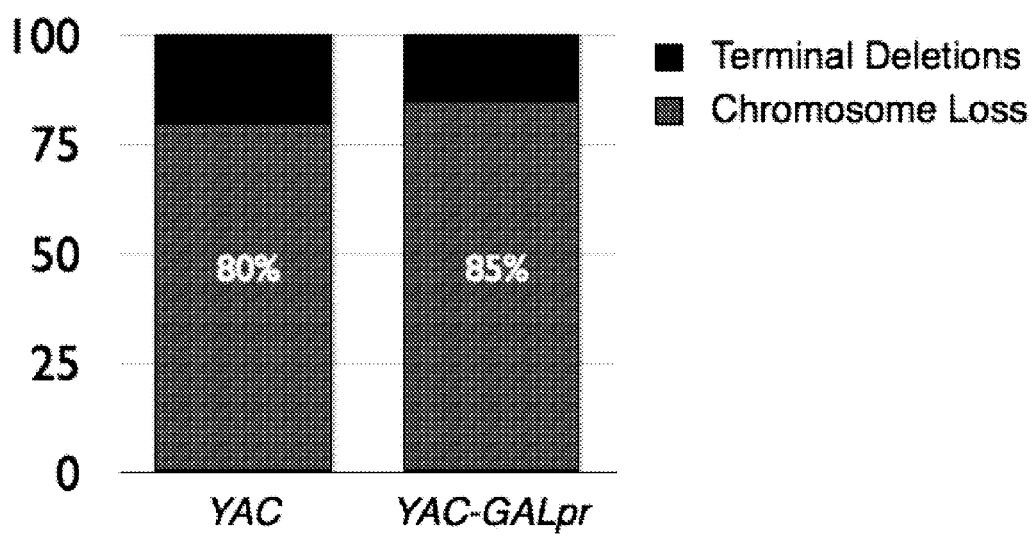
FIG. 14. The percent of terminal deletions and chromosome loss events recovered after 5 hours of growth in galactose-containing media is comparable for YAC and YAC-GALpr strains.

To determine whether the Rad51p-dependent hybrids induced by YAC-GALpr led to genome instability, the instability of YAC-GALpr upon galactose treatment was monitored. Indeed, its instability was elevated 25-fold with a distribution of chromosome loss and terminal deletions similar to that seen in wild type and RNA biogenesis mutants (FIG. 2; FIG. 14). Furthermore, this transcription-induced YAC instability was suppressed by over-expression of RNAse H or deletion of RAD51 (FIG. 2d-e). Thus both by DIP and YAC instability, hybrids induced by transcription at the model YAC-GALpr locus, like those induced by RNA biogenesis mutants, required Rad51p for their formation.

Rad51p Binding at Site of Hybrid Formation

Figure 15:
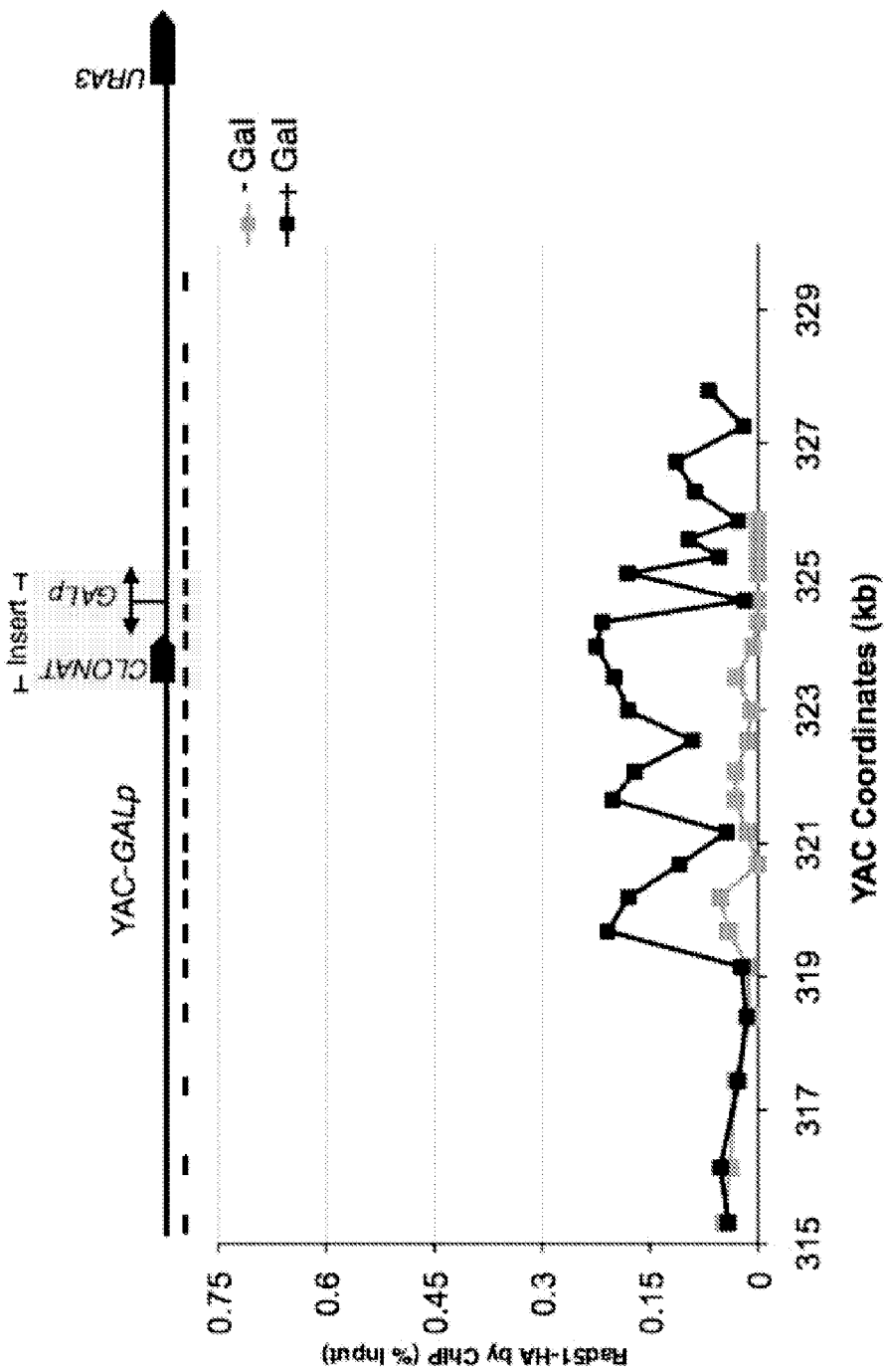
FIG. 15. Rad51p binding is detectable around the YAC-GALpr module upon induction of transcription.
Figure 16:
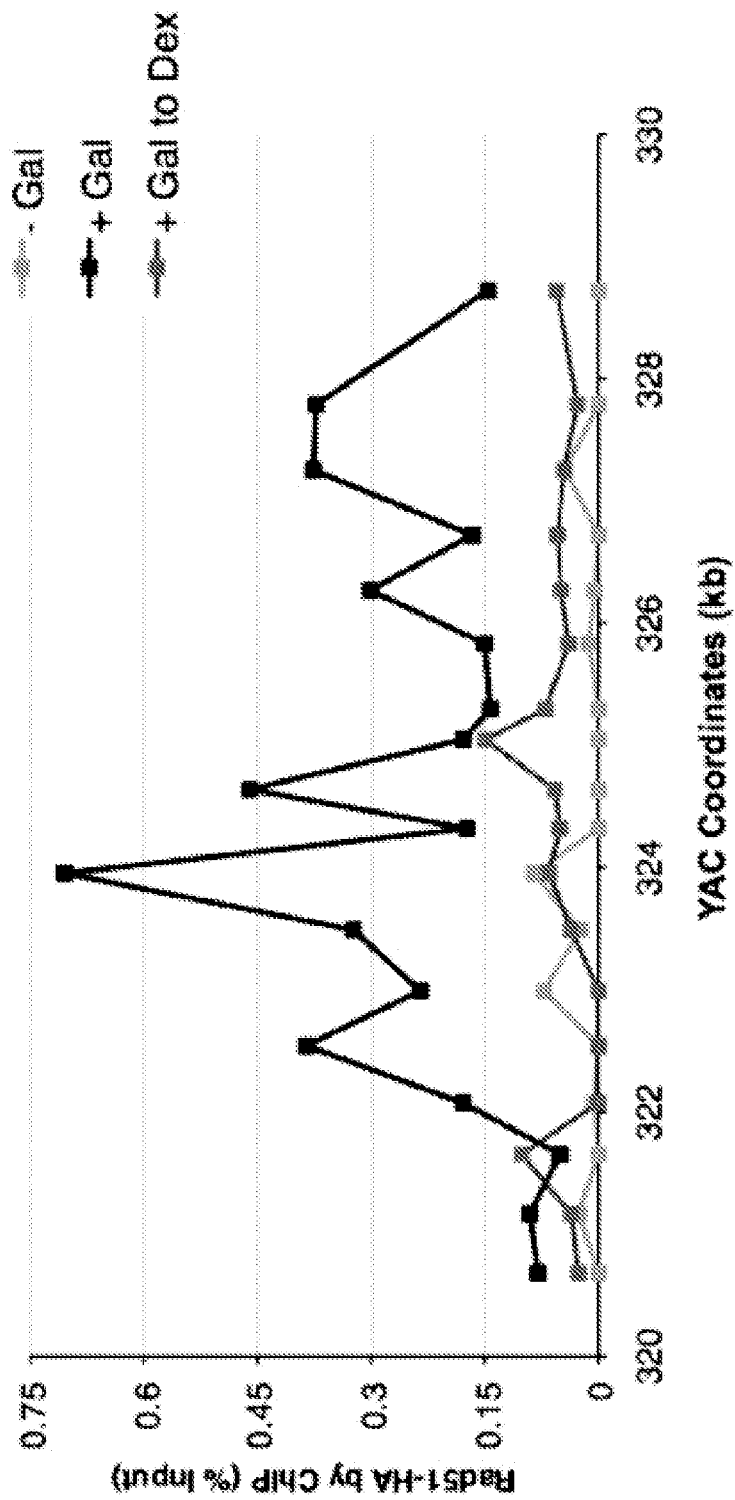
FIG. 16. Rad51p binding is reduced around the YAC-GALpr module upon return to repressive conditions.

A second prediction of Rad51p-mediated hybrid formation is that Rad51p should be detectable near sites of hybrid formation. To test this prediction we used our YAC-GALpr model locus to assay for the presence of Rad51p binding around the site of hybrid formation. Cultures of strains containing the YAC or YAC-GALpr that had been grown in the presence or absence of galactose were generated. These cultures were fixed and assayed for Rad51p binding to the YAC sequences by chromatin immunoprecipitation (ChIP) (See Methods). ChIP was performed using two independent antibodies, anti-HA against a C-terminal haemagglutinin (HA) tagged Rad51p and a polyclonal rabbit anti-Rad51p. No Rad51p binding was detected either on YAC-GALpr in the absence of galactose or on the YAC in the presence or absence of galactose (FIG. 3a). Thus level of Rad51p binding to the YAC or vector sequences in the absence of transcription was very low if any. In contrast, using either antibody for ChIP, significant Rad51p binding was detected around the GAL promoter on YAC-GALpr upon the addition of galactose and induction of transcription (FIG. 3a, FIG. 15). Notably, Rad51p binding appears to extend further than the region of hybrid formation detected by DIP (FIG. 3a and FIG. 2c). Rad51p is known to spread from regions of ssDNA into dsDNA (Zaitsev and Kowalczykowski, 2000), and it's possible that in our model locus Rad51p is spreading from the ssDNA or RNA-DNA hybrid into the neighboring dsDNA. To test further the correlation of transcription and Rad51p binding, dextrose was added to the galactose-treated YAC-GALpr cultures to repress galactose-induced YAC-GALpr transcription (see Methods). In these cultures, Rad51p binding disappeared (FIG. 16). Taken together, Rad51p binding to the region of the hybrid-forming locus on the YAC GALpr was observed only when transcripts from this region are induced. Interestingly, the region of Rad51p binding on the YAC-GALpr is larger than the region of galactose-induced transcription as defined by our qRT-PCR analysis and hybrid formation as defined by DIP.

It is proposed that the binding of Rad51p observed at the model locus is due to its role in hybrid formation. However, hybrids are thought to induce double-strand breaks (DSBs), and Rad51p binds at DSBs to initiate DNA repair through homologous recombination ((Sugawara et al., 2003), FIG. 17A). Therefore, the presence of Rad51p at the hybrid-forming locus might be due to its function in repair rather than in hybrid formation. To address this alternative explanation for Rad51p binding, molecular and functional tests for the formation of DSBs two hours after the induction of transcription were performed. As a molecular assay, we monitored a 20 Kb region surrounding the GAL promoter for the accumulation of phosphorylated histone H2AX ($\gamma$-H2AX) by ChIP. This modification is one of the most dramatic and earliest markers of DSB formation, arising within minutes and spanning large regions of chromatin adjacent to the break ((Shroff et al., 2004), FIG. 17B). However, a ChIP signal for $\gamma$-H2AX ChIP above background level was not detected In the YAC-GALpr strain even under conditions that induced Rad51p binding (FIG. 3b). Thus by this molecular assay Rad51p binding occurs at the site of hybrid formation prior to hybrid-induced DNA damage.

As a functional test, the fact that adding dextrose after two hours suppressed transcription and Rad51p binding at the model hybrid locus was taken advantage of. It was proposed that if Rad51p binding during the two hours prior to the addition of dextrose reflected Rad51p association with hybrid-induced DNA damage, then this damage would manifest as increased YAC instability. However, no increase in YAC instability was observed (FIG. 18), indicating that binding of Rad51p to this locus during the first two hours was unlikely to result from DNA damage. Thus neither our molecular nor functional test supports the binding of Rad51p to the model locus prior to hybrid-induced DNA damage, pointing to a direct role of the Rad51p in hybrid formation.

It was next evaluated whether the formation of all hybrids requires Rad51p. Studies suggest that hybrids not only form in RNA biogenesis mutants but also transiently in wild-type cells (Mischo et al., 2011a; Wahba et al., 2011). The latter fail to persist because of their rapid removal by RNases H and Sen1 (Mischo et al., 2011b; Wahba et al., 2011). To test whether these naturally occurring hybrids are also dependent on Rad51p, hybrid staining and YAC instability in rnh1Δrnh201Δ in the absence of RAD51 was monitored. Neither hybrid staining nor YAC instability was suppressed (FIG. 4a, b), indicating that the transient hybrids in wild-type cells are not Rad51p dependent. Thus both Rad51p-dependent and -independent mechanisms for hybrid formation exist.

Rad51p-Dependent Hybrid Formation can Occur in Trans

In the in vitro bacterial studies, RecA promoted hybrid formation in the absence of active transcription, suggesting that RNA-DNA hybrids can form post-transcriptionally, or in trans. To test whether in vivo hybrids could form in trans, we constructed a strain, LW7003, in which chromosome III contained a 3.5 Kb of vector and human sequences surrounding the galactose promoter of the YAC-GALpr (henceforth referred to as the YAC-GALpr module). This strain also contained the original unmodified YAC, allowing testing of whether transcription of the YAC-GALpr module on chromosome III could induce both hybrid formation on the YAC and YAC instability (FIG. 5a).

To test directly whether hybrids can form in trans, DIP was performed on cultures of our LW7003 strain after growth in the presence or absence of galactose. One primer set that monitored hybrids from both the YAC and YAC-GALpr module generated a strong DIP signal only in the presence of galactose (FIG. 5b, primer 1). This combined hybrid signal was eliminated when the rad51Δ was introduced in this strain (FIG. 5b, primer 1). These results minimally corroborate our previous demonstration of hybrids forming in cis and show that hybrid formation is dependent upon Rad51p.

Figure 19:
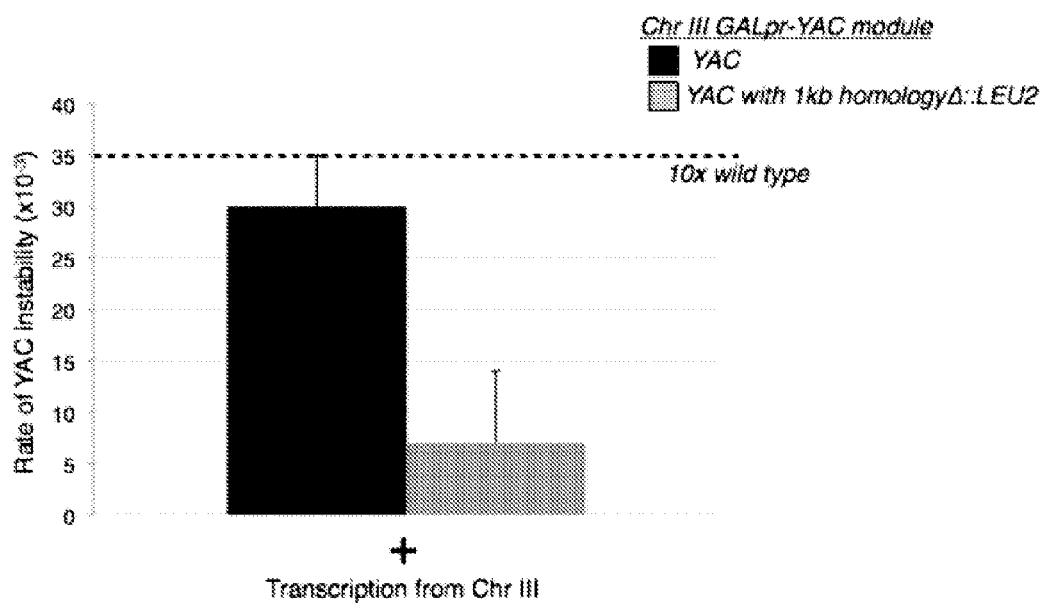
FIG. 19. Levels of YAC instability in the trans assay with and without a region of homology on the YAC.

Two other primer sets that monitored hybrids only from the YAC also revealed a strong DIP signal only in the presence of galactose (FIG. 5b, primer 2 and 3). These results demonstrated transcription-dependent hybrid formation in trans. This trans-specific hybrid signal was eliminated when rad51Δ was introduced into our strain. The RAD51-dependent DIP results strongly support the formation of Rad51p-dependent hybrids in trans.

hybrid formation on the YAC in trans was also tested for by monitoring YAC instability in LW7003. As expected no increase in YAC instability was observed in this strain in the absence of galactose (FIG. 6a). However YAC instability increased 10 fold upon galactose-induced transcription of the YAC-GALpr module on chromosome III, (FIG. 6a, black bars). The transcription-induced YAC instability was dependent on the homology between the YAC and the transcribed YAC sequences from the YAC-GALpr module on chromosome III, as deletion of the corresponding 1 kb of homology from the YAC completely suppressed the transcription-induced YAC instability (FIG. 19). The elevated YAC instability was blocked by RNase H over-expression, indicating the YAC instability was hybrid dependent (FIG. 6a, grey bars). YAC instability was also blocked after introduction of the rad51Δ in LW7003 (FIG. 6b). Thus transcription from the YAC-GALpr module on chromosome III acted in trans to cause the YAC to rearrange through a hybrid- and Rad51p-dependent mechanism.

If the YAC instability induced by the YAC-GALpr module on chromosome III is mediated by hybrids formed in trans on the YAC, then these hybrids should lead to a similar distribution of YAC loss and terminal deletion as hybrids induced in cis. Indeed hybrids induced in trans and in cis both lead to a similar distribution of YAC instability events; on average 85% are HIS– URA– (chromosome loss) and 15% are HIS+ URA– (putative terminal deletions). However, the total rate of YAC instability increased only 10 fold by hybrids formed in trans (from the YAC-GALpr module on chromosome III) compared to 25 fold by hybrids formed in cis. Thus, hybrid formation in trans may be less efficient than in cis.

Figure 20:
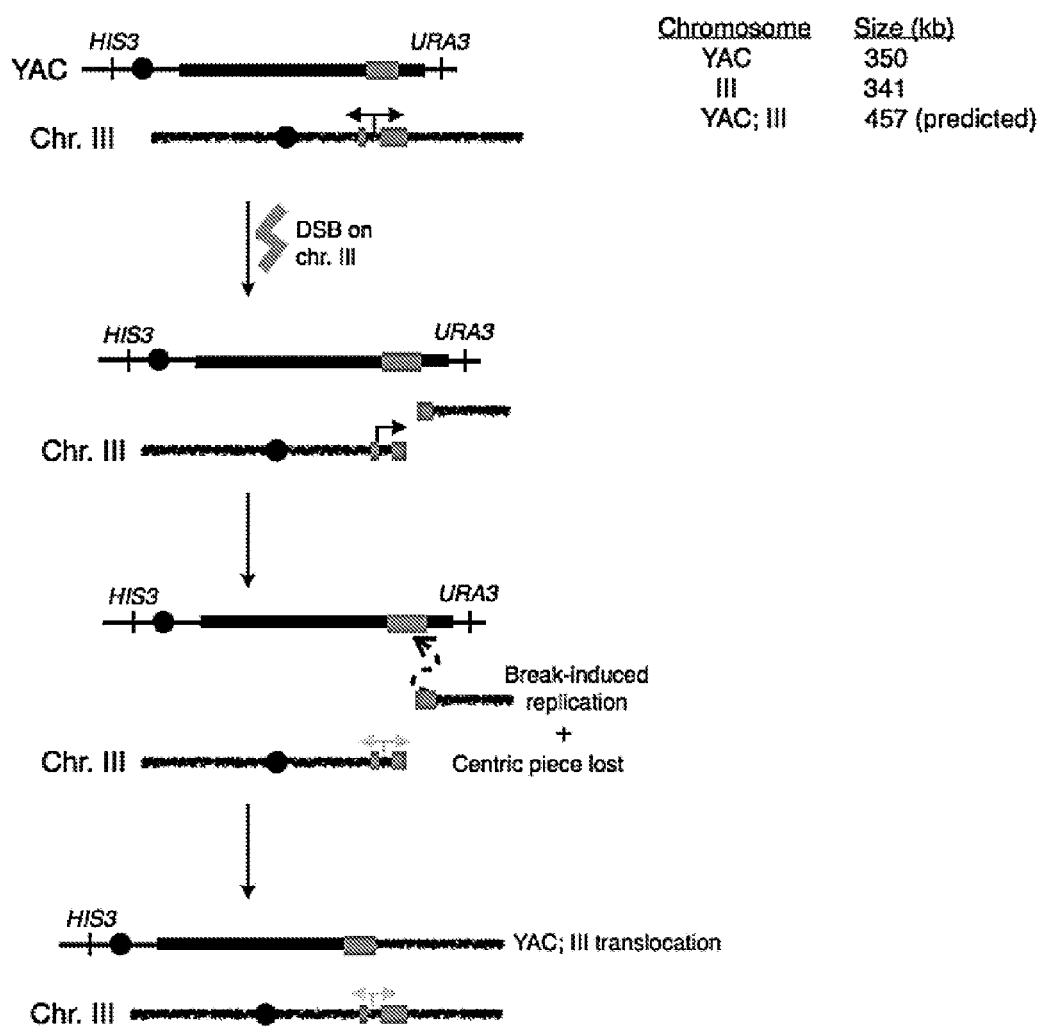
FIG. 20. Schematic representation of an alternative for how His+Ura− colonies may arise in the trans assay.

While it was assumed that HIS+ URA– clones of LW7003 reflect terminal deletions of the YAC, these clones may have had rearrangements that occurred by an indirect mechanism as a result of hybrid-induced double strand breaks in cis. In this model hybrids would form in cis at the module on chromosome III and cause DSBs there. These DSBs in cis would induce recombination between the YAC sequences on the broken chromosome III and the YAC, resulting in a chromosome III; YAC translocation that has the same genetic phenotype (HIS+ URA–) as YAC terminal deletions (FIG. 20). To determine what fraction of rearrangements may have occurred by this indirect mechanism, pulse-field gel and Southern analysis on DNA isolated from ten independent HIS+ URA– colonies of LW7003 was performed. Amongst the 10 YAC rearrangements analyzed, nine were shorter than the existing YAC consistent with the formation of YAC terminal deletions (FIG. 6c). Only one rearrangement was the size expected if a chromosome III; YAC translocation. Thus the structure of most rearranged YACs in LW7003 is consistent with the formation of terminal deletions through the formation of hybrids in trans. These results further support our hypothesis that hybrids can form in trans by a Rad51p mechanism, causing chromosome instability at sites distinct from the site of hybrid RNA transcription.

Enhancers and Repressors of Rad51p Modulate Hybrid Formation

During homologous recombination, the activity of Rad51p is regulated by a number of factors that modulate Rad51p binding to ssDNA and dsDNA (Krejci et al., 2003; Sugawara et al., 2003). Because of the importance of such accessory factors for Rad51p function, we wondered whether they might also help regulate Rad51 in hybrid formation. To test this, positive and negative regulators of Rad51-DNA filament formation were deleted.

Figure 21:
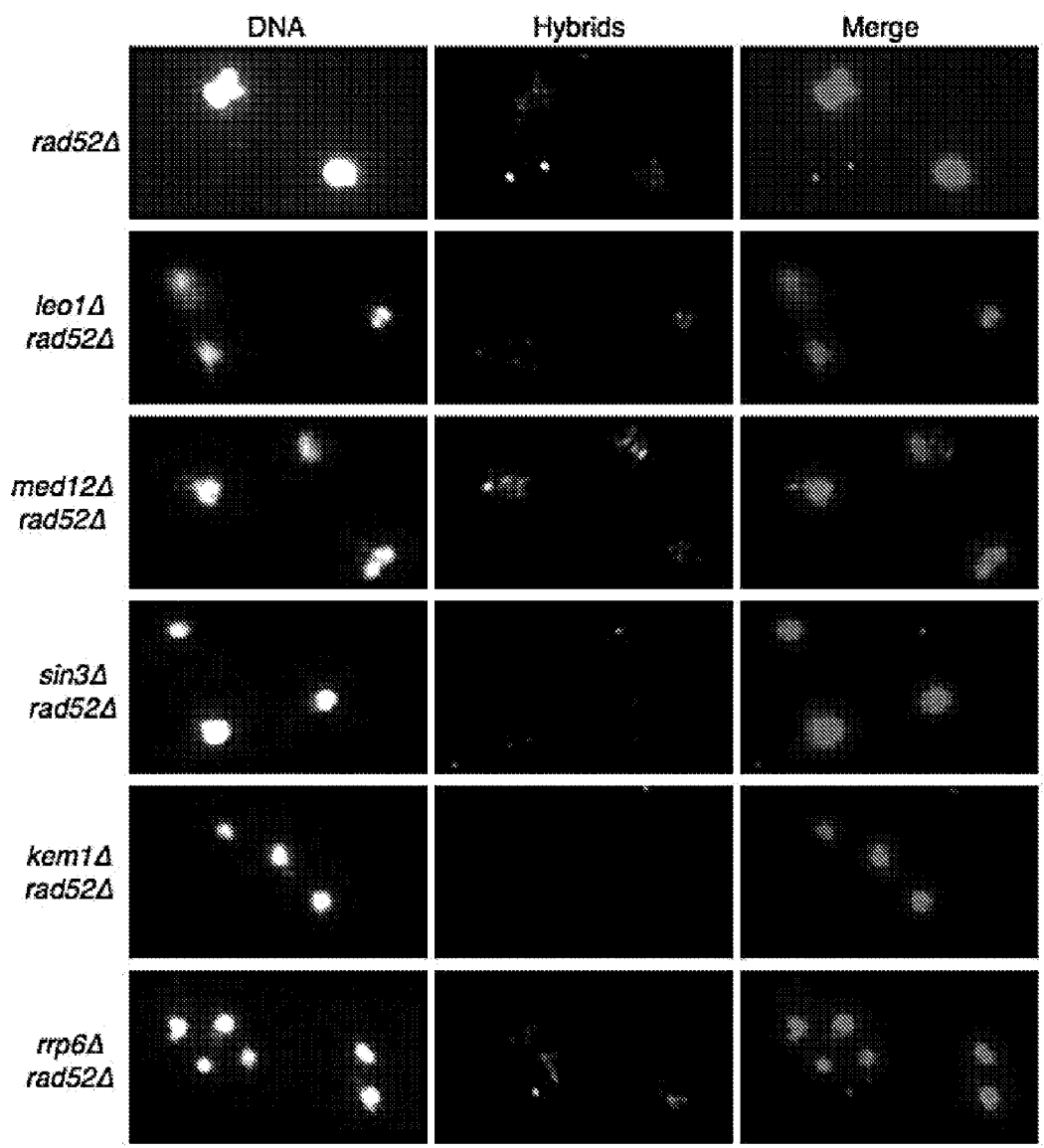
FIG. 21. Larger panels of chromatin spreads showing multiple nuclei of rad52Δ mutants stained with S9.6 antibody.

Rad52p is required for the binding of Rad51p to ssDNA (FIG. 7a, (Song and Sung, 2000)). Deletion of RAD52 (rad52Δ) in our panel of transcriptional mutants completely suppressed hybrid staining, as assayed by chromosome spreads (FIG. 7b, FIG. 21). Note that it was not possible to test suppression of YAC instability in the double mutants because the rad52Δ alone caused substantial hybrid-independent YAC instability, an expected result given its central role in many repair pathways. Nonetheless, the suppression of hybrid staining by rad52Δ suggests that hybrid formation is not simply a consequence of a rogue activity of Rad51p but rather occurs as part of the canonical Rad51p repair pathway.

A number of inhibitors of Rad51p have been identified. SRS2 is a helicase involved in removing Rad51p filaments formed on ssDNA (Krejci et al., 2003), and Rad54p and Rdh54p are two translocases that promote the removal of Rad51p from double-stranded DNA (Shah et al., 2010). It was tested whether these inhibitors might help suppress the rogue hybrid-forming activity of the Rad51p pathway in wild-type cells. To test this we deleted SRS2, RAD54 and RDH54 from cells and measured hybrid formation and YAC instability. Neither single nor double deletions of RAD54 and RDH54 significantly increased hybrid formation or YAC instability (FIGS. 8a and 8b, FIG. 22). In contrast, deletion of SRS2 increased both hybrid staining and YAC instability. Both of these phenotypes of the srs2Δ were suppressed in the srs2Δ rad51Δ mutant (FIG. 8c). Thus, Srs2p antagonizes the hybrid-forming activity of the Rad51p pathway and represents another mechanism by which cells protect their genome against hybrid formation.

The hybrid staining pattern in srs2Δ nuclei was reminiscent of the pattern observed in sin3Δ cells, exhibiting an apparent enrichment of RNA-DNA hybrids at the RDN locus on chromosome XII, the site of 150 tandem rDNA copies (Wahba et al., 2011). We measured rDNA instability by monitoring the rate of excision of a URA3 marker inserted at the RDN locus (Heidinger-Pauli et al., 2010). In srs2Δ cells, the rate of rDNA instability is 23-fold over wild type, a marked increase in instability as compared to the 4-fold increase in YAC instability (FIGS. 8c and 8d). Together these results suggest that Srs2p has a particularly important role in protecting the highly transcribed rDNA locus against Rad51p-dependent hybrid formation and repeat instability.

FIG. 1. Deletion of RAD51 suppresses RNA-DNA hybrids and YAC instability. (A) left panel—Representative images of chromatin spreads stained with S9.6 antibody, showing reduced RNA-DNA hybrid staining in mutants with a deletion of RAD51 (rad51Δ). Right panel—Percent of total nuclei scored that stain positively for RNA-DNA hybrid in chromatin spreads is quantified. 50-100 nuclei from two independent experiments were scored for each genotype. (B) Rate of YAC instability in mutants is also reduced when RAD51 is deleted. Error bars represent standard deviation calculated from at least 4 independent colonies.

FIG. 2. Hybrid-mediated YAC instability is induced in wild-type when high rates of transcription are induced on the YAC using the GAL1-10 promoter (GALpr). (A) Schematic of the YAC-GALpr construct. Total YAC length is 350 kb, of which 324 kb come from human chromosome VII. The GALpr was integrated 10 kb from the telomere, on the arm with the URA3 marker. (B) Quantitative RT-PCR monitoring changes in RNA levels on the YAC 5 hours post induction with galactose. YAC RNA is normalized to actin RNA, and represented as fold change, as compared to RNA levels detected in uninduced cells. Above the table is a schematic representation of the YAC region from which RNA is measured, with the qRT-PCR fragments used in quantification indicated with black dashes. The region in grey represents the GAL1-10 promoter and selectable marker integrated in the YAC-GALpr strain. (C) DIP analysis to monitor RNA-DNA hybrid formation in the YAC-GALpr strain in the absence of galactose, and 2 hours post induction with galactose. Error bars represent standard deviation calculated from two independent DIP experiments. (D) Rates of YAC instability in strains with YAC (black bars) or YAC-GALpr (grey bars) 5 hours after addition of galactose to the media. Strains carried either an RNase H over-expressing plasmid, or an empty control vector. (E) Induced YAC instability is suppressed when RAD51 is deleted. Error bars represent standard deviation calculated from at least three independent colonies.

Figure 3:
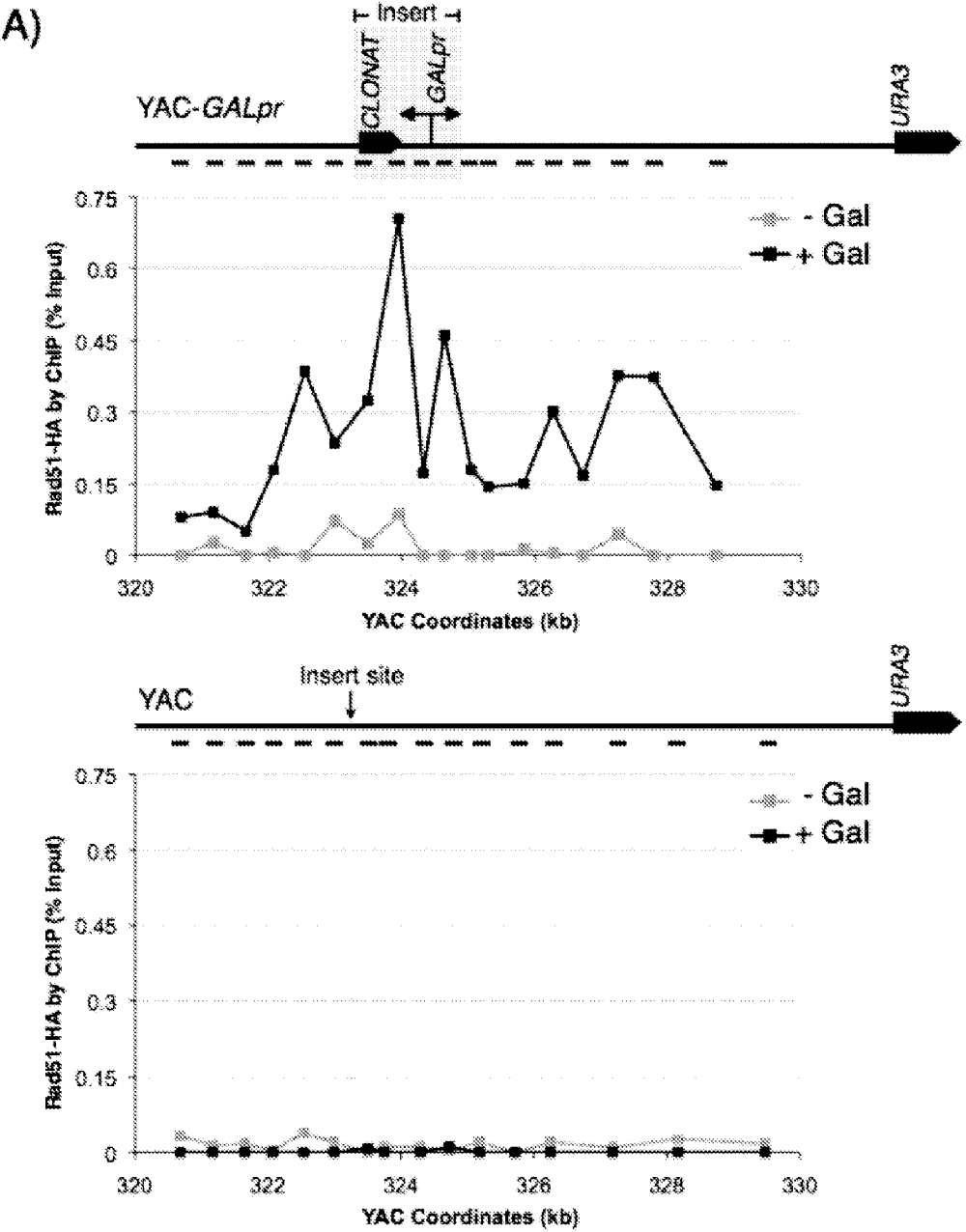
FIG. 3. Rad51p binding is detectable around the YAC-GALpr module upon induction of transcription.
Figure 3:
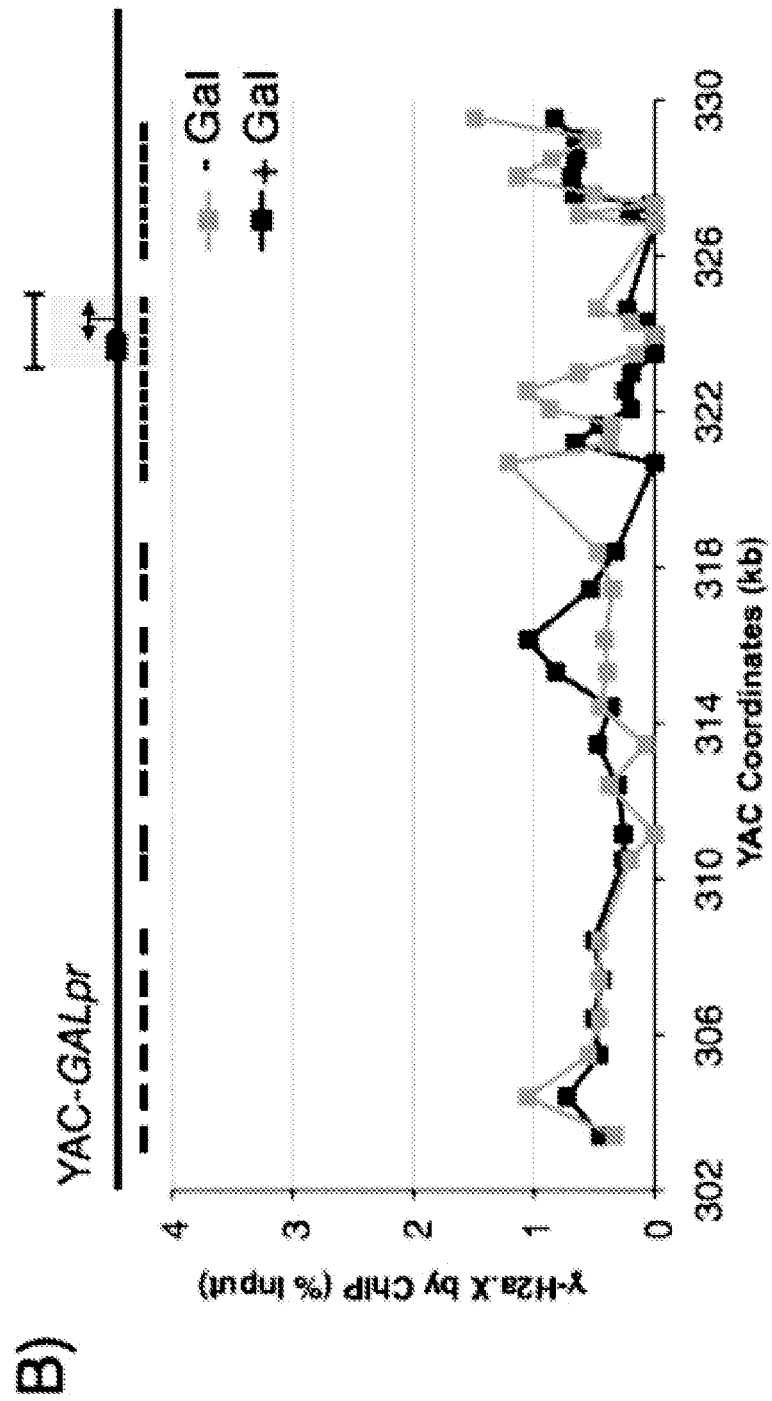

FIG. 3. Rad51p binding is detectable around the YAC-GALpr module upon induction of transcription. Cells growing exponentially in YEP-lactic acid were split, and galactose added to one half. The other half was collected immediately for the −Gal sample and fixed for chromatin immunoprecipitation (ChIP, see Materials and Methods). After 120 minutes, the +Gal sample was similarly fixed for ChIP. Input DNA and DNA coimmunprecipitated with α-HA or -γ-H2a.X (IP) antibody were amplified using primer sets along the YAC as annotated with black dashes on the YAC-GALpr or YAC schematic above each graph. (A) ChIP of Rad51-HA in the YAC-GALpr strain shows an increased signal in Rad51-HA binding 2 hours after induction of transcription by addition of galactose to the media (top panel). No change in RAD51-HA signal is observed in the YAC strain (bottom pane). A (B) ChIP of γ-H2a.X in YAC-GALpr reveals no significant change in signal within 2 hours of galactose induction.

Figure 4:
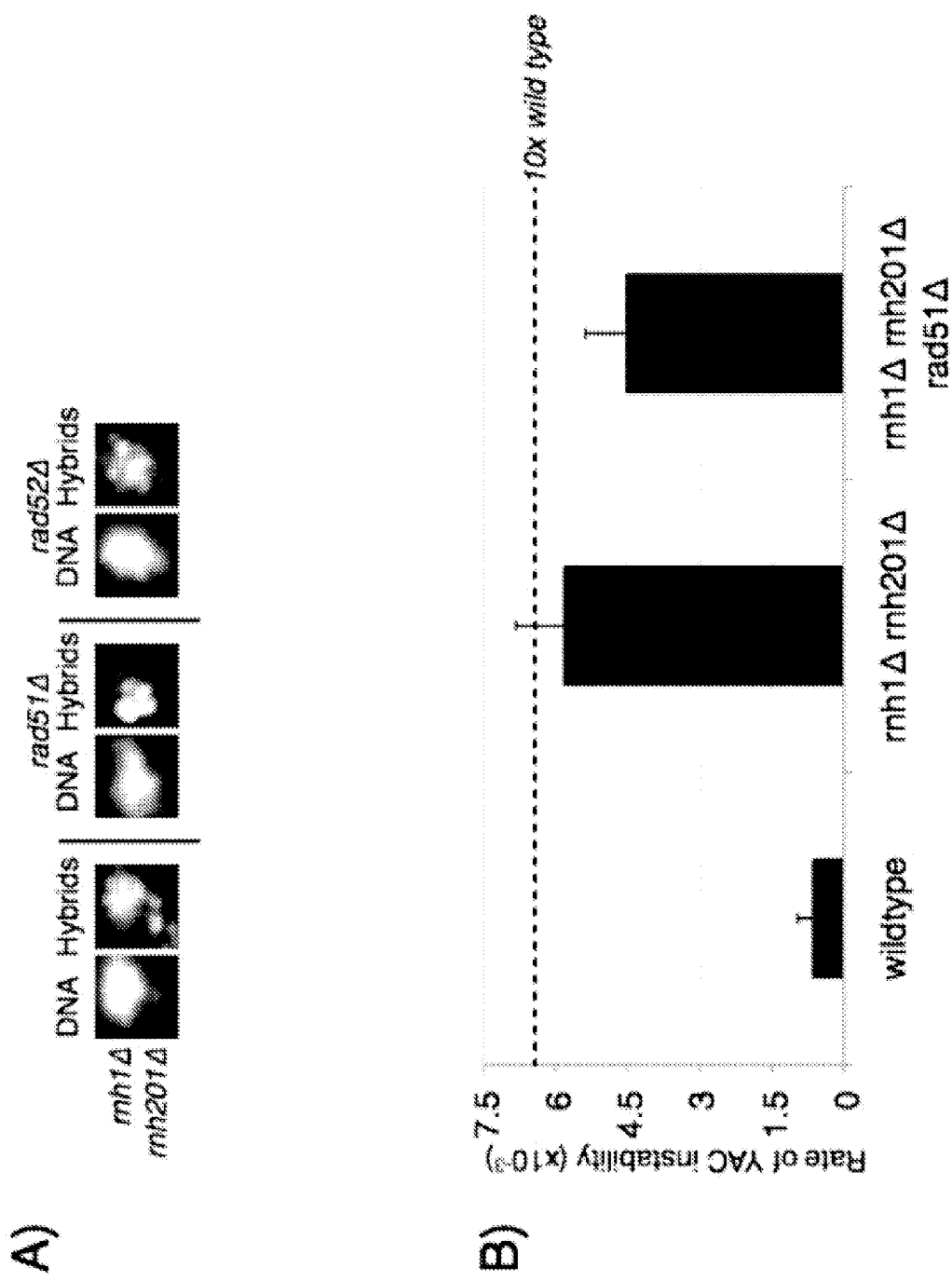
FIG. 4. Deletions of RAD51 and RAD52 do not affect RNA-DNA hybrid formation in rnh1Δrnh201Δ.

FIG. 4. Deletions of RAD51 and RAD52 do not affect RNA-DNA hybrid formation in rnh1Δrnh201Δ. (A) Representative images of chromatin spreads stained with S9.6 antibody. (B) Rate of YAC instability is similar in rnh1Δrnh201Δ and strains lacking RAD51 (rad51Δ) or RAD52 (rad52Δ). Error bars represent standard deviation calculated from at least 6 independent colonies.

Figure 5:
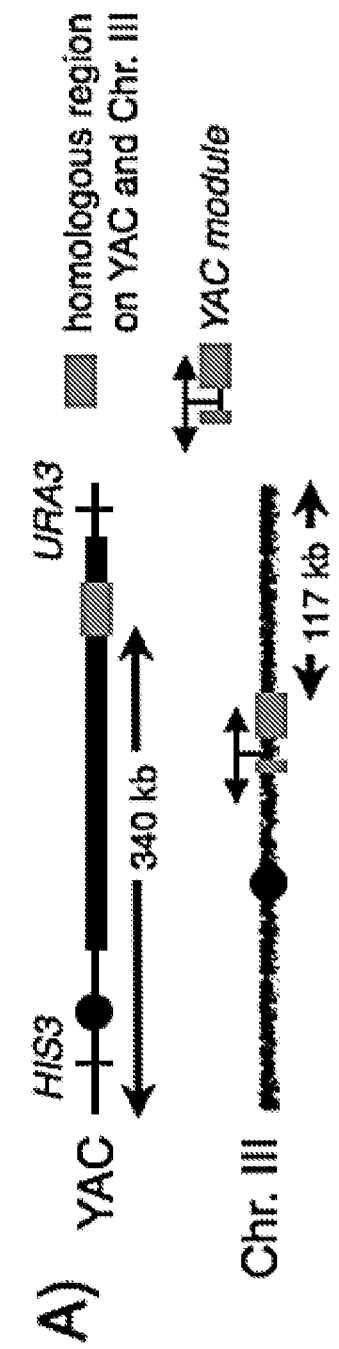
FIG. 5. Transcription of YAC sequences transform chromosome III causes RNA-DNA hybrid formation in trans on the YAC.

FIG. 5. Transcription of YAC sequences transform chromosome III causes RNA-DNA hybrid formation in trans on the YAC. (A) Schematic representation of the trans assay is depicted. The GALpr, selectable marker (Clonat), and a total of 1.1 kb of YAC DNA was integrated on chromosome III. (B) Schematic representation of where the primer sets used to monitor hybrid formation in trans are depicted. Hybrid formation is monitored by DIP 2 hours post induction with galactose in RAD51 and rad51Δ strains. Error bars represent standard deviation from two independent experiments.

Figure 6:
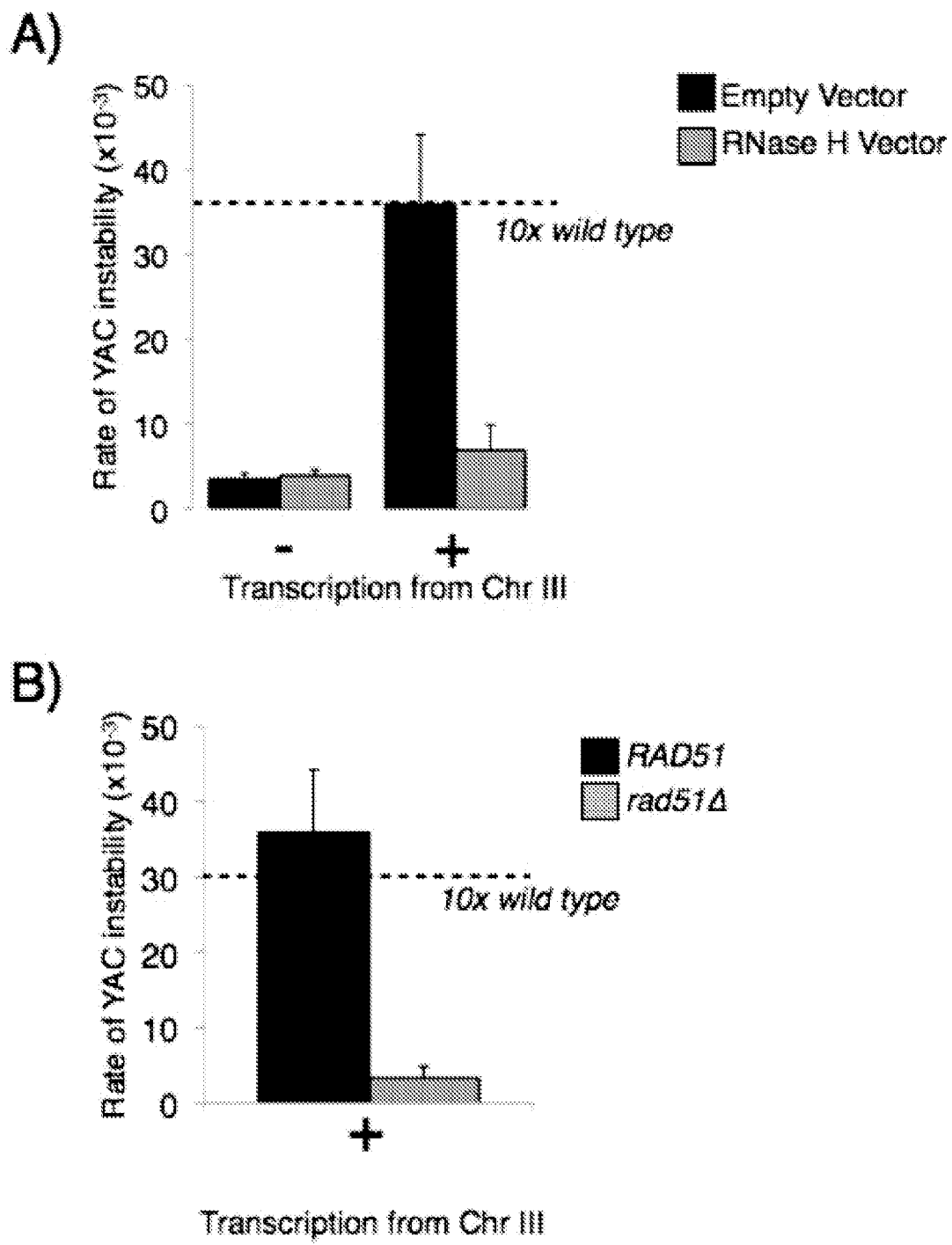
FIG. 6. Transcription of YAC sequences in trans causes hybrid-mediated YAC instability.
Figure 6:
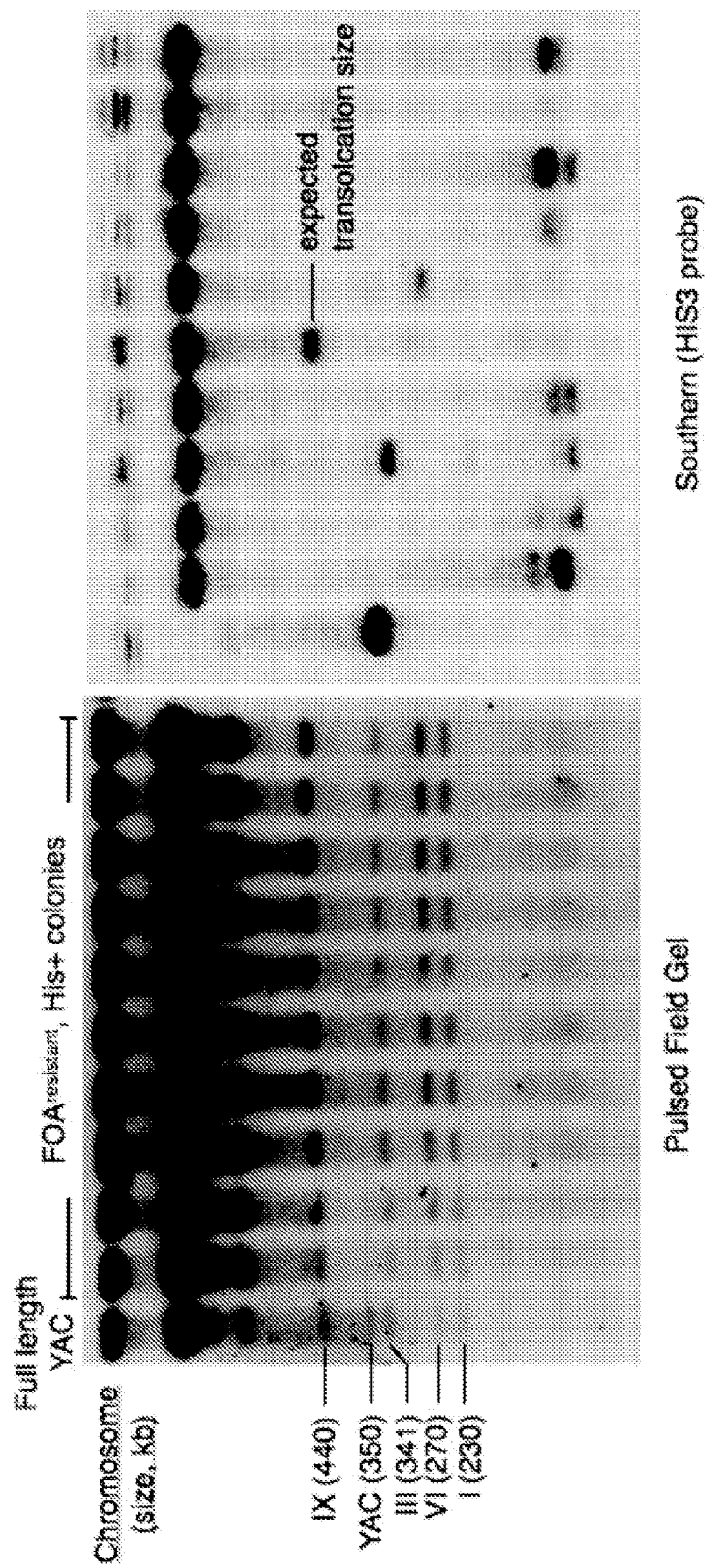

FIG. 6. Transcription of YAC sequences in trans causes hybrid-mediated YAC instability. (A) Rates of YAC instability in strains carrying an empty control vector (black bars) or RNAse H over-expressing vector (grey bars) showing an increased rate of instability upon induction of transcription, that is reduced when RNAse H is over-expressed. Error bars represent standard deviation calculated from at least 3 independent colonies. (B) Rate of YAC instability is suppressed when RAD51 is knocked out. (C) Pulse-field gel and Southern analysis with HIS3 probe of FOA$^{resistant}$, His+ colonies, showing that 9/10 colonies analyzed have YACs rearranged to a smaller size.

Figure 7:
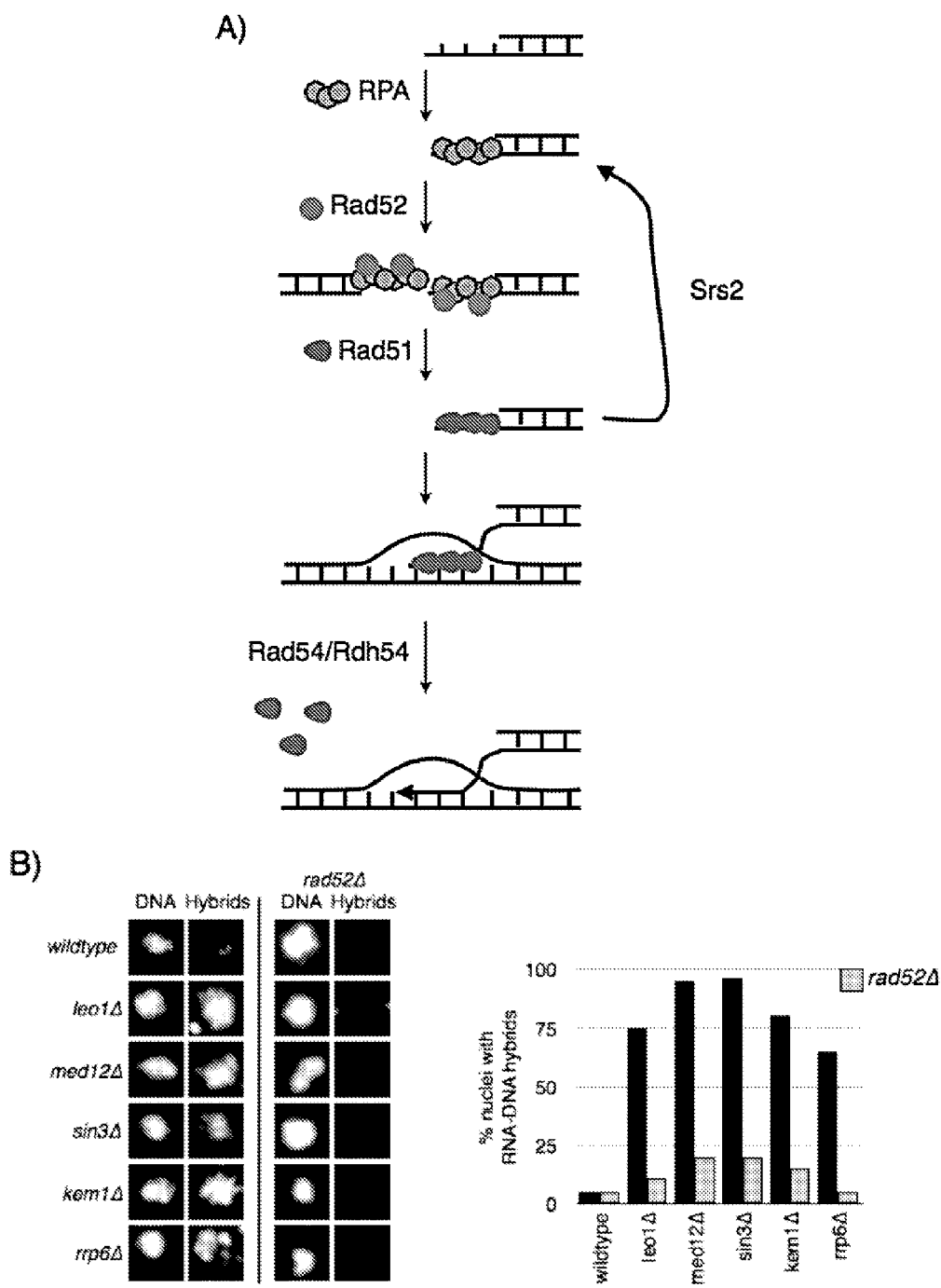
FIG. 7. Deletion of RAD52 suppresses RNA-DNA hybrids.

FIG. 7. Deletion of RAD52 suppresses RNA-DNA hybrids. (A) Schematic showing the major proteins canonically involved in regulating Rad51p binding in DNA repair. Following resection, Replication Protein A (RPA) polymerizes onto ssDNA. Rad52 then interacts with RPA, and catalyzes its exchange for Rad51p. The Rad51-ssDNA filament promotes the pairing and strand exchange reaction with a homologous region in duplex DNA. Srs2p, Rad54p and Rdh54p all regulate the Rad51 filament by dismantling Rad51 from ssDNA and dsDNA, respectively. (B) Representative images of chromatin spreads stained with S9.6 antibody and quantification of nuclei, showing reduced RNA-DNA hybrid staining in mutants with RAD52 knocked out. 50-100 nuclei from two independent experiments were scored for each genotype.

FIG. 8. Deletion of SRS2, but not RAD54 and RDH54 increases genome instability and hybrid formation. (A) Rate of YAC instability is increased in srs2Δ, but not in rad54Δ and rdh54Δ single and double mutants. Error bars represent standard deviation calculated from at least 6 independent colonies. (B) Representative images of chromatin spreads stained with S9.6 antibody, showing increased RNA-DNA hybrid staining in srs2Δ. (C) Left panel-Rate of YAC instability in srs2Δ is suppressed when RAD51 is knocked out. Right panel—Hybrid staining is also reduced in the srs2Δ rad51Δ double mutant. (D) srs2Δ mutants with URA3 integrated at the rDNA were assayed for loss of the URA3 marker, showing increased instability. Error bars represent standard deviation calculated from at least 6 independent colonies.

Figure 9:
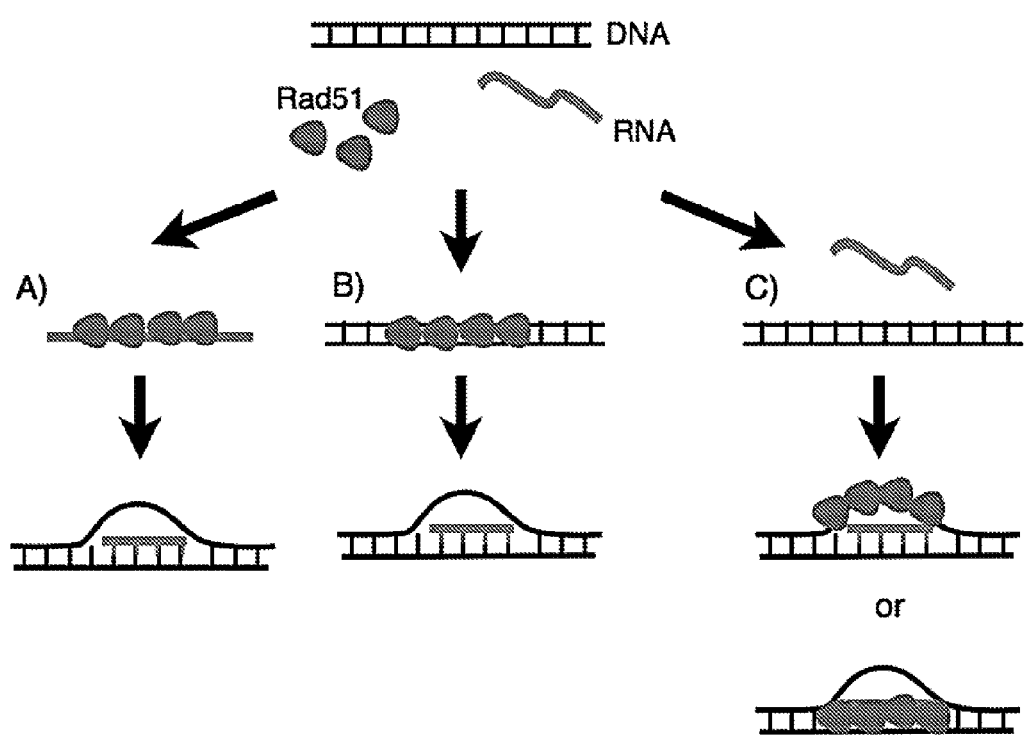
FIG. 9. Three models for how Rad51p may mediate RNA-DNA hybrid formation.

FIG. 9. Three models for how Rad51p may mediate RNA-DNA hybrid formation. (A) In the forward reaction Rad51p polymerizes onto RNA, and mediates strand exchange with homologous DNA, forming an RNA-DNA hybrid. (B) In the inverse reaction, Rad51p forms a filament on dsDNA, and promotes strand exchange with homologous RNA. (C) A third alternative is that Rad51 forms a filament on the extruded ssDNA, stabilizing an open D-loop that allows RNA to bind to homologous sequences.

FIG. 10. Larger panels of chromatin spreads showing multiple nuclei of single mutants stained with S9.6 antibody.

FIG. 11. Larger panels of chromatin spreads showing multiple nuclei of double mutants stained with S9.6 antibody.

FIG. 12. Dot blotting with S9.6 antibody. Roughly 1 μg of DNA from indicated genotypes was spotted onto the membrane and stained with the S9.6 antibody. As a reference known amounts of pre-formed RNA-DNA hybrids were also spotted. Pre-formed RNA-DNA hybrids were made by performing a first strand synthesis reaction on total RNA. Amounts were quantified using Quant-iT Picogreen (Invitrogen).

Figure 13:
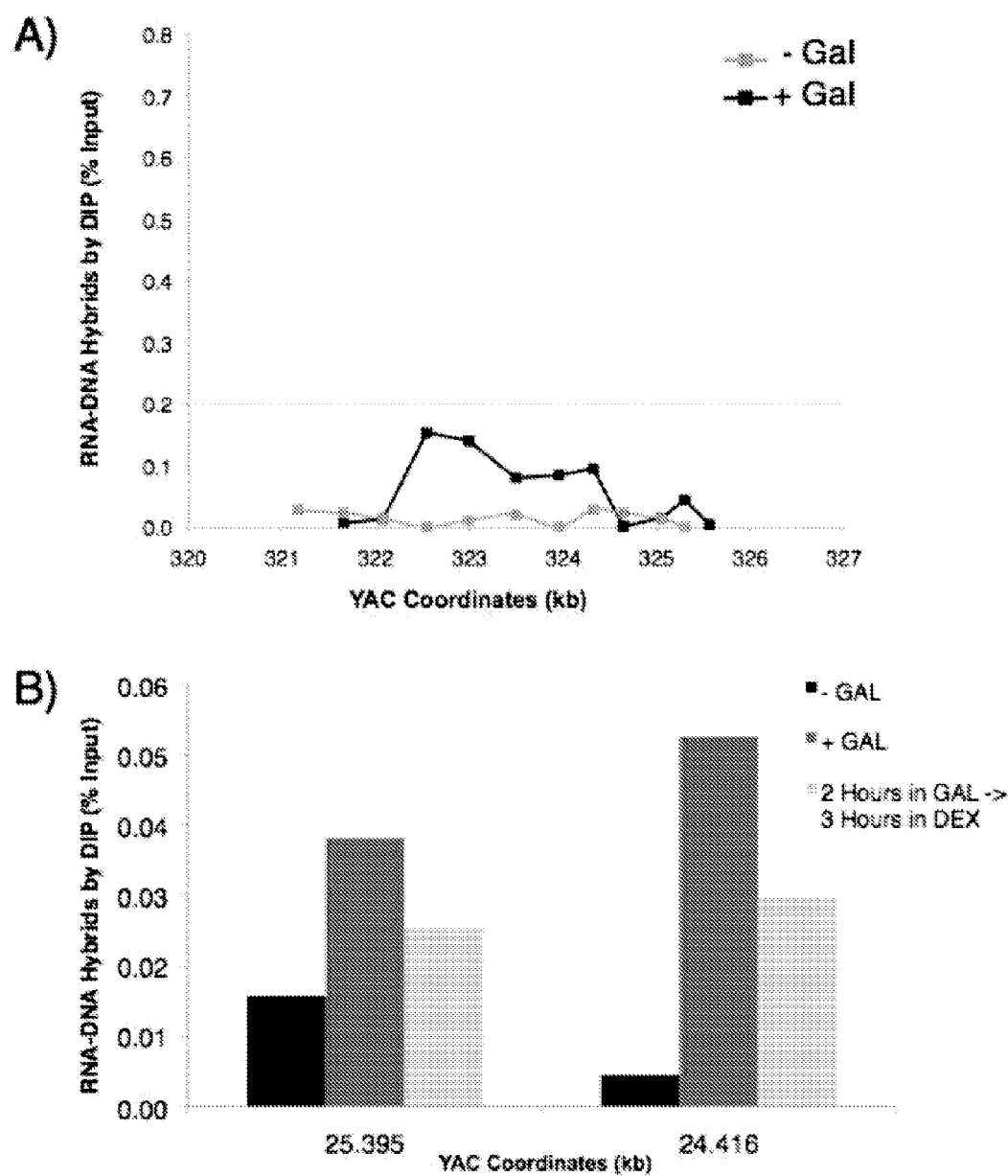
FIG. 13. (A) DIP analysis of YAC strain prior to and 2 hours post addition of galactose to the media. (B) Monitoring of DIP signal in the YAC-GALpr strain at a distal region, showing low levels of hybrid signal upon induction with galactose as compared to. (C) DIP signals are reduced around the YAC-GALpr module upon return to repressive conditions.
Figure 13:
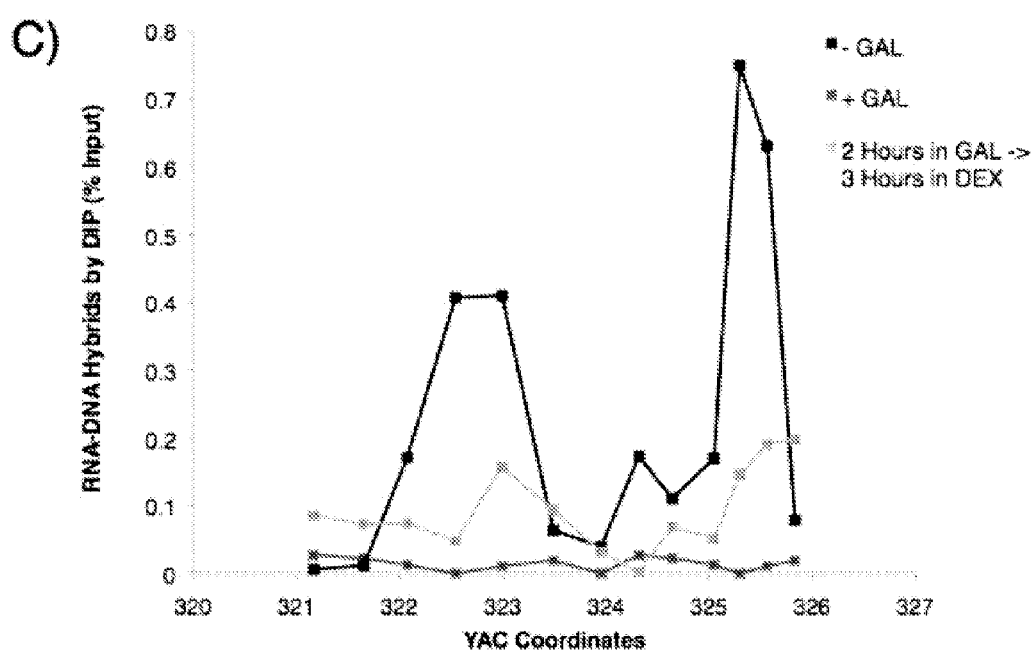

FIG. 13. (A) DIP analysis of YAC strain prior to and 2 hours post addition of galactose to the media. (B) Monitoring of DIP signal in the YAC-GALpr strain at a distal region, showing low levels of hybrid signal upon induction with galactose as compared to. (C) DIP signals are reduced around the YAC-GALpr module upon return to repressive conditions.

FIG. 14. The percent of terminal deletions and chromosome loss events recovered after 5 hours of growth in galactose-containing media is comparable for YAC and YAC-GALpr strains.

FIG. 15. Rad51p binding is detectable around the YAC-GALpr module upon induction of transcription. ChIP of untagged Rad51 using a polyclonal antibody, showing an increased signal in Rad51 binding 2 hours after induction of transcription with galactose.

FIG. 16. Rad51p binding is reduced around the YAC-GALpr module upon return to repressive conditions. After 2 hours of growth in galactose-containing media, dextrose was then added to the media, and cells were allowed to grow, maintained in exponential phase, for 3 hours. Cells were then fixed and used for ChIP of Rad51-HA.

FIG. 17. Rad51 and γ-H2a.X binding at an inducible break site on Chromosome III. (A) ChIP of Rad51-V5 around a double-strand break induced by a site-specific HO endonuclease under control of a galactose inducible promoter. The graph shows levels of Rad51-V5 binding prior to, and 2 hours after adding galactose to the media. (B) ChIP of γ-H2a.X around the break site prior to, and 2 hours after adding galactose to the media.

Figure 18:
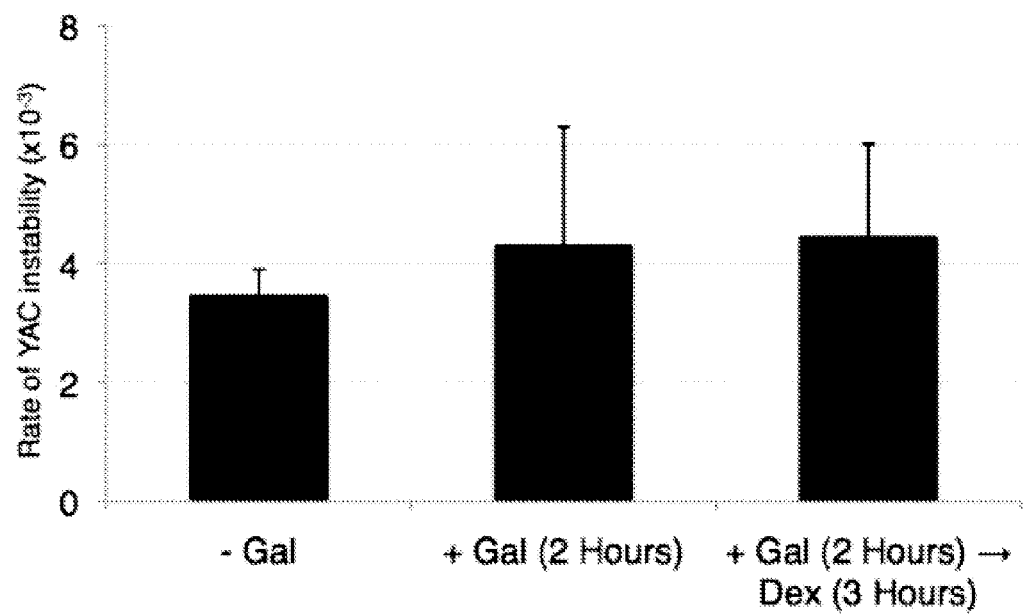
FIG. 18. Wild type levels of YAC instability are observed after 2 hours of transcription induction.

FIG. 18. Wild type levels of YAC instability are observed after 2 hours of transcription induction. YAC-GALpr strains were grown for 2 hours in galactose-containing media, followed by addition of dextrose and growth for 3 more hours. Error bars represent standard deviation calculated from 2 independent colonies.

FIG. 19. Levels of YAC instability in the trans assay with and without a region of homology on the YAC. The 1 kb region of the YAC inserted on chromosome III (YAC-GALpr module) was replaced on the YAC with a LEU2 cassette. Wild type levels of YAC instability are observed in that strain after 2 hours of induction with galactose.

FIG. 20. Schematic representation of an alternative for how His+Ura− colonies may arise in the trans assay. Upon induction of transcription, breaks may occur in cis on chromosome III. Repair via break-induced replication, using homologous YAC sequences as a substrate can lead to a chromosome III; YAC translocation.

FIG. 21. Larger panels of chromatin spreads showing multiple nuclei of rad52Δ mutants stained with S9.6 antibody.

FIG. 22. Larger panels of chromatin spreads showing multiple nuclei of srs2Δ and rdh54Δrad54Δ mutants stained with S9.6 antibody. Quantification of number of nuclei that stained positively for RNA-DNA hybrids in srs2Δ and rdh54Δrad54Δ. Total number of nuclei scored is 50-100 per genotype, from two independent experiments.

REFERENCES

Aguilera, A., and García-Muse, T. (2012). R Loops: From Transcription Byproducts to Threats to Genome Stability. Mol Cell 46, 115-124.

Aguilera, A., and Gómez-González, B. (2008). Genome instability: a mechanistic view of its causes and consequences. Nat Rev Genet 9, 204-217.

Alzu, A., Bermejo, R., Begnis, M., Lucca, C., Piccini, D., Carotenuto, W., Saponaro, M., Brambati, A., Cocito, A., Foiani, M., et al. (2012). Senataxin Associates with Replication Forks to Protect Fork Integrity across RNA-Polymerase-II-Transcribed Genes. Cell 151, 835-846.

Burgess, R. C., Lisby, M., Altmannova, V., Krejci, L., Sung, P., and Rothstein, R. (2009). Localization of recombination proteins and Srs2 reveals anti-recombinase function in vivo. J Cell Biol 185, 969-981.

Cao, Y., and Kogoma, T. (1993). Requirement for the polymerization and 5"-->3" exonuclease activities of DNA polymerase I in initiation of DNA replication at oriK sites in the absence of RecA in *Escherichia coli* rnhA mutants. J Bacteriol 175, 7254-7259.

Cheung, V., Chua, G., Batada, N. N., Landry, C. R., Michnick, S. W., Hughes, T. R., and Winston, F. (2008). Chromatin- and transcription-related factors repress transcription from within coding regions throughout the *Saccharomyces cerevisiae* genome. PLoS Biol 6, e277.

DiCarlo, J. E., Norville, J. E., Mali, P., Rios, X., Aach, J., and Church, G. M. (2013). Genome engineering in *Saccharomyces cerevisiae* using CRISPR-Cas systems. Nucleic Acids Res 41, 4336-4343.

Drolet, M. M., Phoenix, P. P., Menzel, R. R., Massé, E. E., Liu, L. F. L., and Crouch, R. J. R. (1995). Overexpression of RNase H partially complements the growth defect of an *Escherichia coli* delta topA mutant: R-loop formation is a major problem in the absence of DNA topoisomerase I. Proc Natl Acad Sci USA 92, 3526-3530.

Ginno, P. A. P., Lott, P. L. P., Christensen, H. C. H., Korf, I. I., and Chédin, F. F. (2012). R-loop formation is a distinctive characteristic of unmethylated human CpG island promoters. Mol Cell 45, 814-825.

Hage, El, A., French, S. L., Beyer, A. L., and Tollervey, D. (2010). Loss of Topoisomerase I leads to R-loop-mediated transcriptional blocks during ribosomal RNA synthesis. Genes & Development 24, 1546-1558.

Heidinger-Pauli, J. M., Mert, O., Davenport, C., Guacci, V., and Koshland, D. (2010). Systematic reduction of cohesin differentially affects chromosome segregation, condensation, and DNA repair. Curr Biol 20, 957-963.

Hong, X., Cadwell, G. W., and Kogoma, T. (1995). *Escherichia coli* RecG and RecA proteins in R-loop formation. Embo J 14, 2385-2392.

Huertas, P., and Aguilera, A. (2003). Cotranscriptionally formed DNA: RNA hybrids mediate transcription elongation impairment and transcription-associated recombination. Mol Cell.

Jinek, M., Chylinski, K., Fonfara, I., Hauer, M., Doudna, J. A., and Charpentier, E. (2012). A Programmable Dual-RNA-Guided DNA Endonuclease in Adaptive Bacterial Immunity. Science 337, 816-821.

Kasahara, M., Clikeman, J. A., Bates, D. B., and Kogoma, T. (2000). RecA protein-dependent R-loop formation in vitro. Genes & Development 14, 360-365.

Kim, N., and Jinks-Robertson, S. (2009). dUTP incorporation into genomic DNA is linked to transcription in yeast. Nature 459, 1150-1153.

Krejci, L., Van Komen, S., Li, Y., Villemain, J., Reddy, M. S., Klein, H., Ellenberger, T., and Sung, P. (2003). DNA helicase Srs2 disrupts the Rad51 presynaptic filament. Nature 423, 305-309.

Li, X., and Manley, J. L. (2005). Inactivation of the SR protein splicing factor ASF/SF2 results in genomic instability. Cell 122, 365-378.

Matson, S. W. (1989). *Escherichia coli* DNA helicase II (uvrD gene product) catalyzes the unwinding of DNA.RNA hybrids in vitro. Proc Natl Acad Sci USA 86, 4430-4434.

Mischo, H. E., Gómez-González, B., Grzechnik, P., Rondon, A. G., Wei, W., Steinmetz, L., Aguilera, A., and Proudfoot, N. J. (2011a). Yeast Sen1 Helicase Protects the Genome from Transcription-Associated Instability supplemental. Mol Cell 41, 21-32.

Mischo, H. E., Gómez-González, B., Grzechnik, P., Rondon, A. G., Wei, W., Steinmetz, L., Aguilera, A., and Proudfoot, N. J. (2011b). Yeast Sen1 Helicase Protects the Genome from Transcription-Associated Instability. Mol Cell 41, 21-32.

Nakama, M., Kawakami, K., Kajitani, T., Urano, T., and Murakami, Y. (2012). DNA-RNA hybrid formation mediates RNAi-directed heterochromatin formation. Genes to Cells 17, 218-233.

Paulsen, R. D., Soni, D. V., Wollman, R., Hahn, A. T., Yee, M.-C., Guan, A., Hesley, J. A., Miller, S. C., Cromwell, E. F., Solow-Cordero, D. E., et al. (2009). A genome-wide siRNA screen reveals diverse cellular processes and pathways that mediate genome stability. Mol Cell 35, 228-239.

Richardson, C., Stark, J. M., Ommundsen, M., and Jasin, M. (2004). Rad51 overexpression promotes alternative double-strand break repair pathways and genome instability. Oncogene 23, 546-553.

Roy, D., Zhang, Z., Lu, Z., Hsieh, C.-L., and Lieber, M. R. (2010). Competition between the RNA transcript and the nontemplate DNA strand during R-loop formation in vitro: a nick can serve as a strong R-loop initiation site. Mol Cell Biol 30, 146-159.

Schwartz, D. C., and Cantor, C. R. (1984). Separation of yeast chromosome-sized DNAs by pulsed field gradient gel electrophoresis. Cell 37, 67-75.

Shah, P. P., Zheng, X., Epshtein, A., Carey, J. N., Bishop, D. K., and Klein, H. L. (2010). Swi2/Snf2-Related Translocases Prevent Accumulation of Toxic Rad51 Complexes during Mitotic Growth. Mol Cell 39, 862-872.

Shroff, R. R., Arbel-Eden, A. A., Pilch, D. D., Ira, G. G., Bonner, W. M. W., Petrini, J. H. J., Haber, J. E. J., and Lichten, M. M. (2004). Distribution and Dynamics of Chromatin Modification Induced by a Defined DNA Double-Strand Break. Curr Biol 14, 9-9.

Song, B., and Sung, P. (2000). Functional interactions among yeast Rad51 recombinase, Rad52 mediator, and replication protein A in DNA strand exchange. J Biol Chem 275, 15895-15904.

Stirling, P. C., Chan, Y. A., Minaker, S. W., Aristizabal, M. J., Barrett, I., Sipahimalani, P., Kobor, M. S., and Hieter, P. (2012). R-loop-mediated genome instability in mRNA cleavage and polyadenylation mutants. Genes & Development 26, 163-175.

Sugawara, N., Wang, X., and Haber, J. E. (2003). In vivo roles of Rad52, Rad54, and Rad55 proteins in Rad51-mediated recombination. Mol Cell 12, 209-219.

Sung, P. (1994). Catalysis of ATP-dependent homologous DNA pairing and strand exchange by yeast RAD51 protein. Science (New York, N.Y.) 265, 1241-1243.

Tuduri, S., Crabbé, L., Conti, C., Tourrière, H., Holtgreve-Grez, H., Jauch, A., Pantesco, V., De Vos, J., Thomas, A., Theillet, C., et al. (2009). Topoisomerase I suppresses genomic instability by preventing interference between replication and transcription. Nature Cell Biology 11, 1315-1324.

Unal, E., Arbel-Eden, A., Sattler, U., Shroff, R., Lichten, M., Haber, J. E., and Koshland, D. (2004). DNA damage response pathway uses histone modification to assemble a double-strand break-specific cohesin domain. Mol Cell 16, 991-1002.

Wahba, L., Amon, J. D., Koshland, D., and Vuica-Ross, M. (2011). RNase H and Multiple RNA Biogenesis Factors Cooperate to Prevent RNA:DNA Hybrids from Generating Genome Instability. Mol Cell 44, 978-988.

Wyers, F., Rougemaille, M., Badis, G., Rousselle, J.-C., Dufour, M.-E., Boulay, J., Régnault, B., Devaux, F., Namane, A., Séraphin, B., et al. (2005). Cryptic pol II transcripts are degraded by a nuclear quality control pathway involving a new poly(A) polymerase. Cell 121, 725-737.

Zaitsev, E. N., and Kowalczykowski, S. C. (2000). A novel pairing process promoted by *Escherichia coli* RecA protein: inverse DNA and RNA strand exchange. Genes & Development 14, 740-749.

Zhou, B. B., and Elledge, S. J. (2000). The DNA damage response: putting checkpoints in perspective. Nature 408, 433-439.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for increasing the efficiency of site specific cleavage of a target DNA, the method comprising contacting the target DNA with:
   a) a complex comprising a Cas9 polypeptide and a guide RNA, wherein the guide RNA comprises a first segment comprising a nucleotide sequence that is complementary to a sequence in the target DNA and a second segment that binds to the Cas9 polypeptide; and
   b) an amount of a Rad51 polypeptide sufficient to enhance binding of the first segment to the target DNA.

2. The method of claim 1, wherein the method is an in vitro method.

3. The method of claim 1, wherein the method is an in vivo method and wherein the target DNA is comprised within a living cell.

4. The method of claim 3, wherein the Rad51 polypeptide is heterologous to the cell.

5. The method of claim 3, wherein the cell modified in the in vivo method has been genetically modified to comprise a heterologous nucleic acid that comprises a nucleotide coding sequence encoding the Rad51 polypeptide.

6. The method of claim 5, wherein the nucleotide sequence is operably linked to a promoter that is functional in the cell.

7. The method of claim 5, wherein said genetic modification provides for a level of Rad51 that is at least 10% higher than the level of Rad51 polypeptide in a control cell not genetically modified with a heterologous nucleic acid that comprises a nucleotide sequence encoding the Rad51 polypeptide.

* * * * *

SEQUENCE LISTING

<160> NUMBER OF SEQ ID NOS: 76

<210> SEQ ID NO 1
<211> LENGTH: 1366
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile

```
                35                  40                  45
Gly Ala Leu Leu Phe Asp Ser Gly Glu Thr Ala Glu Ala Thr Arg Leu
                        55                  60
 50
Lys Arg Thr Ala Arg Arg Tyr Thr Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Asp Val Asp Lys Leu Phe Ile Gln Leu Val Gln Thr Tyr Asn
                180                 185                 190
Gln Leu Phe Glu Glu Asn Pro Ile Asn Ala Ser Gly Val Asp Ala Lys
                195                 200                 205
Ala Ile Leu Ser Ala Arg Leu Ser Lys Ser Arg Arg Leu Glu Asn Leu
210                 215                 220
Ile Ala Gln Leu Pro Gly Glu Lys Lys Asn Gly Leu Phe Gly Asn Leu
225                 230                 235                 240
Ile Ala Leu Ser Leu Gly Leu Thr Pro Asn Phe Lys Ser Asn Phe Asp
                245                 250                 255
Leu Ala Glu Asp Ala Lys Leu Gln Leu Ser Lys Asp Thr Tyr Asp Asp
                260                 265                 270
Asp Leu Asp Asn Leu Leu Ala Gln Ile Gly Asp Gln Tyr Ala Asp Leu
                275                 280                 285
Phe Leu Ala Ala Lys Asn Leu Ser Asp Ala Ile Leu Leu Ser Asp Ile
                290                 295                 300
Leu Arg Val Asn Thr Glu Ile Thr Lys Ala Pro Leu Ser Ala Ser Met
305                 310                 315                 320
Ile Lys Arg Tyr Asp Glu His His Gln Asp Leu Thr Leu Leu Lys Ala
                325                 330                 335
Leu Val Arg Gln Gln Leu Pro Glu Lys Tyr Lys Glu Ile Phe Phe Asp
                340                 345                 350
Gln Ser Lys Asn Gly Tyr Ala Gly Tyr Ile Asp Gly Gly Ala Ser Gln
                355                 360                 365
Glu Glu Phe Tyr Lys Phe Ile Lys Pro Ile Leu Glu Lys Met Asp Gly
                370                 375                 380
Thr Glu Glu Leu Leu Val Lys Leu Asn Arg Glu Asp Leu Leu Arg Lys
385                 390                 395                 400
Gln Arg Thr Phe Asp Asn Gly Ser Ile Pro His Gln Ile His Leu Gly
                405                 410                 415
Glu Leu His Ala Ile Leu Arg Arg Gln Glu Asp Phe Tyr Pro Phe Leu
                420                 425                 430
Lys Asp Asn Arg Glu Lys Ile Glu Lys Ile Leu Thr Phe Arg Ile Pro
                435                 440                 445
Tyr Tyr Val Gly Pro Leu Ala Arg Gly Asn Ser Arg Phe Ala Trp Met
                455                 460
 450
```

```
Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
            485                 490                 495

Phe Asp Lys Asn Leu Pro Asn Gly Lys Val Leu Pro Lys His Ser Leu
        500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
                595                 600                 605

Glu Glu Asn Glu Asp Ile Leu Glu Asp Ile Val Leu Thr Leu Thr Leu
610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
                660                 665                 670

Gln Ser Gly Lys Thr Ile Leu Asp Phe Leu Lys Ser Asp Gly Phe Ala
                675                 680                 685

Asn Arg Asn Phe Met Gln Leu Ile His Asp Asp Ser Leu Thr Phe Lys
        690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Leu Lys Asp
            835                 840                 845

Asp Ser Ile Asp Asn Lys Val Leu Thr Arg Ser Asp Lys Asn Arg Gly
        850                 855                 860

Lys Ser Asp Asn Val Pro Ser Glu Glu Val Val Lys Lys Met Lys Asn
865                 870                 875                 880
```

```
Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                1000                1005

Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr
            1025                1030                1035

Ser Asn Ile Met Asn Phe Phe Lys Thr Glu Ile Thr Leu Ala Asn
            1040                1045                1050

Gly Glu Ile Arg Lys Arg Pro Leu Ile Glu Thr Asn Gly Glu Thr
            1055                1060                1065

Gly Glu Ile Val Trp Asp Lys Gly Arg Asp Phe Ala Thr Val Arg
            1070                1075                1080

Lys Val Leu Ser Met Pro Gln Val Asn Ile Val Lys Lys Thr Glu
            1085                1090                1095

Val Gln Thr Gly Gly Phe Ser Lys Glu Ser Ile Leu Pro Lys Arg
            1100                1105                1110

Asn Asp Lys Leu Ile Ala Arg Lys Lys Asp Trp Asp Pro Lys Lys
            1115                1120                1125

Tyr Gly Gly Phe Asp Ser Pro Thr Val Ala Tyr Ser Val Leu Val
            1130                1135                1140

Val Ala Lys Val Glu Lys Gly Lys Ser Lys Lys Leu Lys Ser Val
            1145                1150                1155

Lys Glu Leu Leu Gly Ile Thr Ile Met Glu Arg Ser Ser Phe Glu
            1160                1165                1170

Lys Asn Pro Ile Asp Phe Leu Glu Ala Lys Gly Tyr Lys Glu Val
            1175                1180                1185

Lys Lys Asp Leu Ile Ile Lys Leu Pro Lys Tyr Ser Leu Phe Glu
            1190                1195                1200

Leu Glu Asn Gly Arg Lys Arg Met Leu Ala Ser Ala Gly Glu Leu
            1205                1210                1215

Gln Lys Gly Asn Glu Leu Ala Leu Pro Ser Lys Tyr Val Asn Phe
            1220                1225                1230

Leu Tyr Leu Ala Ser His Tyr Glu Lys Leu Lys Gly Ser Pro Glu
            1235                1240                1245

Asp Asn Glu Gln Lys Gln Leu Phe Val Glu Gln His Lys His Tyr
            1250                1255                1260

Leu Asp Glu Ile Ile Glu Gln Ile Ser Glu Phe Ser Lys Arg Val
            1265                1270                1275

Ile Leu Ala Asp Ala Asn Leu Asp Lys Val Leu Ser Ala Tyr Asn
```

```
            1280                1285               1290
Lys His Arg Asp Lys Pro Ile Arg Glu Gln Ala Glu  Asn Ile Ile
            1295                1300              1305
His Leu Phe Thr Leu Thr Asn Leu Gly Ala Pro Ala  Ala Phe Lys
            1310                1315              1320
Tyr Phe Asp Thr Thr Ile Asp Arg Lys Arg Tyr Thr  Ser Thr Lys
            1325                1330              1335
Glu Val Leu Asp Ala Thr Leu Ile His Gln Ser Ile  Thr Gly Leu
            1340                1345              1350
Tyr Glu Thr Arg Ile Asp Leu Ser Gln Leu Gly Gly  Asp
            1355                1360              1365

<210> SEQ ID NO 2
<211> LENGTH: 339
<212> TYPE: PRT
<213> ORGANISM: Homo sapiens

<400> SEQUENCE: 2

Met Ala Met Gln Met Gln Leu Glu Ala Asn Ala Asp Thr Ser Val Glu
1               5                   10                  15
Glu Glu Ser Phe Gly Pro Gln Pro Ile Ser Arg Leu Glu Gln Cys Gly
            20                  25                  30
Ile Asn Ala Asn Asp Val Lys Lys Leu Glu Glu Ala Gly Phe His Thr
        35                  40                  45
Val Glu Ala Val Ala Tyr Ala Pro Lys Lys Glu Leu Ile Asn Ile Lys
    50                  55                  60
Gly Ile Ser Glu Ala Lys Ala Asp Lys Ile Leu Ala Glu Ala Ala Lys
65                  70                  75                  80
Leu Val Pro Met Gly Phe Thr Thr Ala Thr Glu Phe His Gln Arg Arg
                85                  90                  95
Ser Glu Ile Ile Gln Ile Thr Thr Gly Ser Lys Glu Leu Asp Lys Leu
            100                 105                 110
Leu Gln Gly Gly Ile Glu Thr Gly Ser Ile Thr Glu Met Phe Gly Glu
        115                 120                 125
Phe Arg Thr Gly Lys Thr Gln Ile Cys His Thr Leu Ala Val Thr Cys
130                 135                 140
Gln Leu Pro Ile Asp Arg Gly Gly Gly Glu Gly Lys Ala Met Tyr Ile
145                 150                 155                 160
Asp Thr Glu Gly Thr Phe Arg Pro Glu Arg Leu Leu Ala Val Ala Glu
                165                 170                 175
Arg Tyr Gly Leu Ser Gly Ser Asp Val Leu Asp Asn Val Ala Tyr Ala
            180                 185                 190
Arg Ala Phe Asn Thr Asp His Gln Thr Gln Leu Leu Tyr Gln Ala Ser
        195                 200                 205
Ala Met Met Val Glu Ser Arg Tyr Ala Leu Leu Ile Val Asp Ser Ala
    210                 215                 220
Thr Ala Leu Tyr Arg Thr Asp Tyr Ser Gly Arg Gly Glu Leu Ser Ala
225                 230                 235                 240
Arg Gln Met His Leu Ala Arg Phe Leu Arg Met Leu Leu Arg Leu Ala
                245                 250                 255
Asp Glu Phe Gly Val Ala Val Val Ile Thr Asn Gln Val Val Ala Gln
            260                 265                 270
Val Asp Gly Ala Ala Met Phe Ala Ala Asp Pro Lys Lys Pro Ile Gly
        275                 280                 285
```

```
Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp

<210> SEQ ID NO 3
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 3
gagaggctga ggcaggag                                                 18

<210> SEQ ID NO 4
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 4
gaagatagaa ccctgaagtc c                                             21

<210> SEQ ID NO 5
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 5
tgacctctct ccccaaac                                                 18

<210> SEQ ID NO 6
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 6
gccaatagta agcaagcag                                                19

<210> SEQ ID NO 7
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 7
agagcaatca gaaaatggta g                                             21

<210> SEQ ID NO 8
<211> LENGTH: 19
<212> TYPE: DNA
<213> ORGANISM: Artificial sequence
<220> FEATURE:
<223> OTHER INFORMATION: synthetic polynucleotide
```

<400> SEQUENCE: 8
tgctcaccta catttcctg					19

<210> SEQ ID NO 9
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 9
gactaaagac cttccgtttg					20

<210> SEQ ID NO 10
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 10
tttgtgtcag gaactaaaca ac				22

<210> SEQ ID NO 11
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 11
gtgatgaggc tggcagtg					18

<210> SEQ ID NO 12
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 12
caaatacttc tacacatcat ccc				23

<210> SEQ ID NO 13
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 13
ttgctggatt ctatttctc					19

<210> SEQ ID NO 14
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 14
tgaaggaaac aaaaccaaag					20

<210> SEQ ID NO 15
<211> LENGTH: 20

```
<212> TYPE: DNA
<213> ORGANISM: Artificial sequence
<220> FEATURE:
<223> OTHER INFORMATION: synthetic polynucleotide

<400> SEQUENCE: 15
ccaaatgctt cccctctctt                                          20

<210> SEQ ID NO 16
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 16
tgtcccctgt attaaggcat tt                                       22

<210> SEQ ID NO 17
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 17
tcagctatcc acccttgacc                                          20

<210> SEQ ID NO 18
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 18
tgcaacctta tttttcagtt cc                                       22

<210> SEQ ID NO 19
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 19
ggagggaccc tgtccatcta                                          20

<210> SEQ ID NO 20
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 20
gggaactaaa tgtgtaggtg gt                                       22

<210> SEQ ID NO 21
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 21
```
agagttccag ggctgtcaaa                                               20

<210> SEQ ID NO 22
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 22
tatggaattc aacttacctt c                                             21

<210> SEQ ID NO 23
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 23
tggatgcagt agtggggagt                                               20

<210> SEQ ID NO 24
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 24
gttaggattt gccactgagg                                               20

<210> SEQ ID NO 25
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 25
acctctggct ggaggtcac                                                19

<210> SEQ ID NO 26
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 26
tggtcgctat actgctgtcg                                               20

<210> SEQ ID NO 27
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 27
tgcaaggcga ttaagttggg                                               20

<210> SEQ ID NO 28
<211> LENGTH: 21
<212> TYPE: DNA
<213> ORGANISM: Artificial sequence

```
<220> FEATURE:
<223> OTHER INFORMATION: synthetic polynucleotide

<400> SEQUENCE: 28
gaggcattaa acacatggta g                                              21

<210> SEQ ID NO 29
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 29
ctaaatcttc attgctccac                                                20

<210> SEQ ID NO 30
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 30
caggttcttg ttgataaggc                                                20

<210> SEQ ID NO 31
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 31
atagcacaca tcaagtggtg                                                20

<210> SEQ ID NO 32
<211> LENGTH: 17
<212> TYPE: DNA
<213> ORGANISM: Artificial sequence
<220> FEATURE:
<223> OTHER INFORMATION: synthetic polynucleotide

<400> SEQUENCE: 32 tccttcctttt tccccctc                                                 17

<210> SEQ ID NO 33
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 33
caaagacaag gtttcatttt c                                              21

<210> SEQ ID NO 34
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 34
caaatgagaa aaataaggtg tgtg                                           24
```

<210> SEQ ID NO 35
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 35
atcttggcaa cggactgc                                                 18

<210> SEQ ID NO 36
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 36
cagccaagaa taagcctatc                                               20

<210> SEQ ID NO 37
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 37
gaataaaact tactgtcatc catc                                          24

<210> SEQ ID NO 38
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 38
ccatacttat ttggagattg c                                             21

<210> SEQ ID NO 39
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 39
gaaaacataa cagcattccc                                               20

<210> SEQ ID NO 40
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 40
acttttattt ctgaactgaa ctgttgg                                       27

<210> SEQ ID NO 41
<211> LENGTH: 19
<212> TYPE: DNA
<213> ORGANISM: Artificial sequence
<220> FEATURE:
<223> OTHER INFORMATION: synthetic polynucleotide

```
<400> SEQUENCE: 41
ccaagccact ggaataaag                                             19

<210> SEQ ID NO 42
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 42
gaggcggaag gtgtagtgag                                            20

<210> SEQ ID NO 43
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 43
tggtttcatc tcaagttttc ca                                         22

<210> SEQ ID NO 44
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 44
tgttgccaaa taaagagaaa caaa                                       24

<210> SEQ ID NO 45
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 45
ccgcatcttc cttttgtagc                                            20

<210> SEQ ID NO 46
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 46
catttttcca acaagagcat gta                                        23

<210> SEQ ID NO 47
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 47
gagaggatgc tgcaaagagc                                            20

<210> SEQ ID NO 48
```

```
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 48
tcaggaagga tgaagaccag a                                          21

<210> SEQ ID NO 49
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 49
agggaatgga gacataaacc                                            20

<210> SEQ ID NO 50
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 50
tgcaggaaac ctggaaacat                                            20

<210> SEQ ID NO 51
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 51
ccaccggcac ctcccgcagg                                            20

<210> SEQ ID NO 52
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 52
cagggcatgc tcatgtagag                                            20

<210> SEQ ID NO 53
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 53
gcctgatgcg gtattttctc                                            20

<210> SEQ ID NO 54
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 54
```
cccgctcggc ggcttctaat c                                                  21

<210> SEQ ID NO 55
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 55
gaggaaatga gctgcatttt c                                                  21

<210> SEQ ID NO 56
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 56
gaaaatgtgc taggcaccgt ac                                                 22

<210> SEQ ID NO 57
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 57
aggcaagtaa gccttttcca                                                    20

<210> SEQ ID NO 58
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 58
cataatgtcc ctaatcctac c                                                  21

<210> SEQ ID NO 59
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 59
tagccctttt cagactctgc                                                    20

<210> SEQ ID NO 60
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 60
taggtcaatg cagcatcagc                                                    20

<210> SEQ ID NO 61
<211> LENGTH: 20
<212> TYPE: DNA

<213> ORGANISM: Artificial sequence
<220> FEATURE:
<223> OTHER INFORMATION: synthetic polynucleotide

<400> SEQUENCE: 61
gttaccaaat ctttctaagc         20

<210> SEQ ID NO 62
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 62
tgttttggta aacattaggc         20

<210> SEQ ID NO 63
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 63
tgctcaaatt cctttcagtc aa         22

<210> SEQ ID NO 64
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 64
tggtgccccg tttataactc         20

<210> SEQ ID NO 65
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 65
ggaccaggct tgacaatgat         20

<210> SEQ ID NO 66
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 66
caagcatgcc ataaatgttc a         21

<210> SEQ ID NO 67
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 67
cccatatttc cccaaataaa g         21

<210> SEQ ID NO 68
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 68
agccaatcta cagactggcc                                              20

<210> SEQ ID NO 69
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 69
tggatgtctg gaaaacagca                                              20

<210> SEQ ID NO 70
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 70
aggcaacaaa catcaaatgg                                              20

<210> SEQ ID NO 71
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 71
gaggaatctc acatgtagag                                              20

<210> SEQ ID NO 72
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 72
tgcgtacgat gcactaggaa                                              20

<210> SEQ ID NO 73
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 73
aaagccagtg gcaaaagaga                                              20

<210> SEQ ID NO 74
<211> LENGTH: 20
<212> TYPE: DNA
<213> ORGANISM: Artificial sequence
<220> FEATURE:

```
<223> OTHER INFORMATION: synthetic polynucleotide

<400> SEQUENCE: 74
attccaaggc caagcataga                                              20

<210> SEQ ID NO 75
<211> LENGTH: 72
<212> TYPE: DNA
<213> ORGANISM: Artificial sequence
<220> FEATURE:
<223> OTHER INFORMATION: synthetic polynucleotide

<400> SEQUENCE: 75
caataccaag gatcccttta gctcttaaag agagacgaca ggatagcaca gatggtcgac   60
tctagaggat cc                                                      72

<210> SEQ ID NO 76
<211> LENGTH: 70
<212> TYPE: DNA
<213> ORGANISM: Artificial sequence
<220> FEATURE:
<223> OTHER INFORMATION: synthetic polynucleotide

<400> SEQUENCE: 76
tatgtgcagc aggatattgg ctgtgctgtt agacaaatcc ttctgtactc cagacctgcg   60
agcagggaaa                                                         70
```